(12) United States Patent
Frei et al.

(10) Patent No.: US 9,750,448 B2
(45) Date of Patent: *Sep. 5, 2017

(54) METHOD, APPARATUS AND SYSTEM FOR VALIDATING AND QUANTIFYING CARDIAC BEAT DATA QUALITY

(71) Applicant: Cyberonics, Inc., Houston, TX (US)

(72) Inventors: Mark G Frei, Leawood, KS (US); Ivan Osorio, Lawrence, KS (US)

(73) Assignee: CYBERONICS, INC., Houston, TX (US)

( * ) Notice: Subject to any disclaimer, the term of this patent is extended or adjusted under 35 U.S.C. 154(b) by 184 days.

This patent is subject to a terminal disclaimer.

(21) Appl. No.: 14/480,406

(22) Filed: Sep. 8, 2014

(65) Prior Publication Data

US 2014/0378851 A1 Dec. 25, 2014

Related U.S. Application Data

(63) Continuation of application No. 12/771,727, filed on Apr. 30, 2010, now Pat. No. 8,831,732, which is a continuation-in-part of application No. 12/770,562, filed on Apr. 29, 2010, now Pat. No. 8,562,536.

(51) Int. Cl.
| | |
|---|---|
| *A61N 1/36* | (2006.01) |
| *A61B 5/00* | (2006.01) |
| *A61B 5/024* | (2006.01) |
| *A61B 5/0245* | (2006.01) |
| *A61B 5/0456* | (2006.01) |

(52) U.S. Cl.
CPC .......... *A61B 5/4094* (2013.01); *A61B 5/0245* (2013.01); *A61B 5/02405* (2013.01); *A61N 1/36053* (2013.01); *A61N 1/36064* (2013.01); *A61N 1/36139* (2013.01); *A61B 5/0456* (2013.01)

(58) Field of Classification Search
CPC .............. A61B 5/4094; A61N 1/36064; A61N 1/36139; A61N 1/36053
USPC .......................................................... 607/45
See application file for complete search history.

(56) References Cited

U.S. PATENT DOCUMENTS 5,738,104 A * 4/1998 Lo ...................... A61B 5/02438
600/509
2010/0274303 A1* 10/2010 Bukhman ............ A61B 5/0452
607/3

* cited by examiner

*Primary Examiner* — Alyssa M Alter
(74) *Attorney, Agent, or Firm* — Williams Morgan, P.C.

(57) ABSTRACT

Methods, systems, and apparatus for quantifying the quality of a fiducial time marker for a candidate heart beat, quantifying the quality of a candidate heart beat, or determining a time of beat sequence of the patient's heart. A fiducial time marker is obtained for a candidate heart beat. A quality index of said candidate heart beat is set to a first value. The candidate heart beat is tested with at least one beat validity test. At least a second value is added to said quality index of said candidate heart beat if said candidate heart beat passes said at least one beat validity test. The candidate heart beat is tested with at least a second heart beat validity test. At least a third value is added to said quality index of said candidate heart beat if said candidate heart beat passes said at least second heart beat validity test. In one class of beat validity test, a constraint defining a pass is modified at one or more times after the most recent prior valid heart beat that is greater than a constraint modification time threshold.

20 Claims, 15 Drawing Sheets

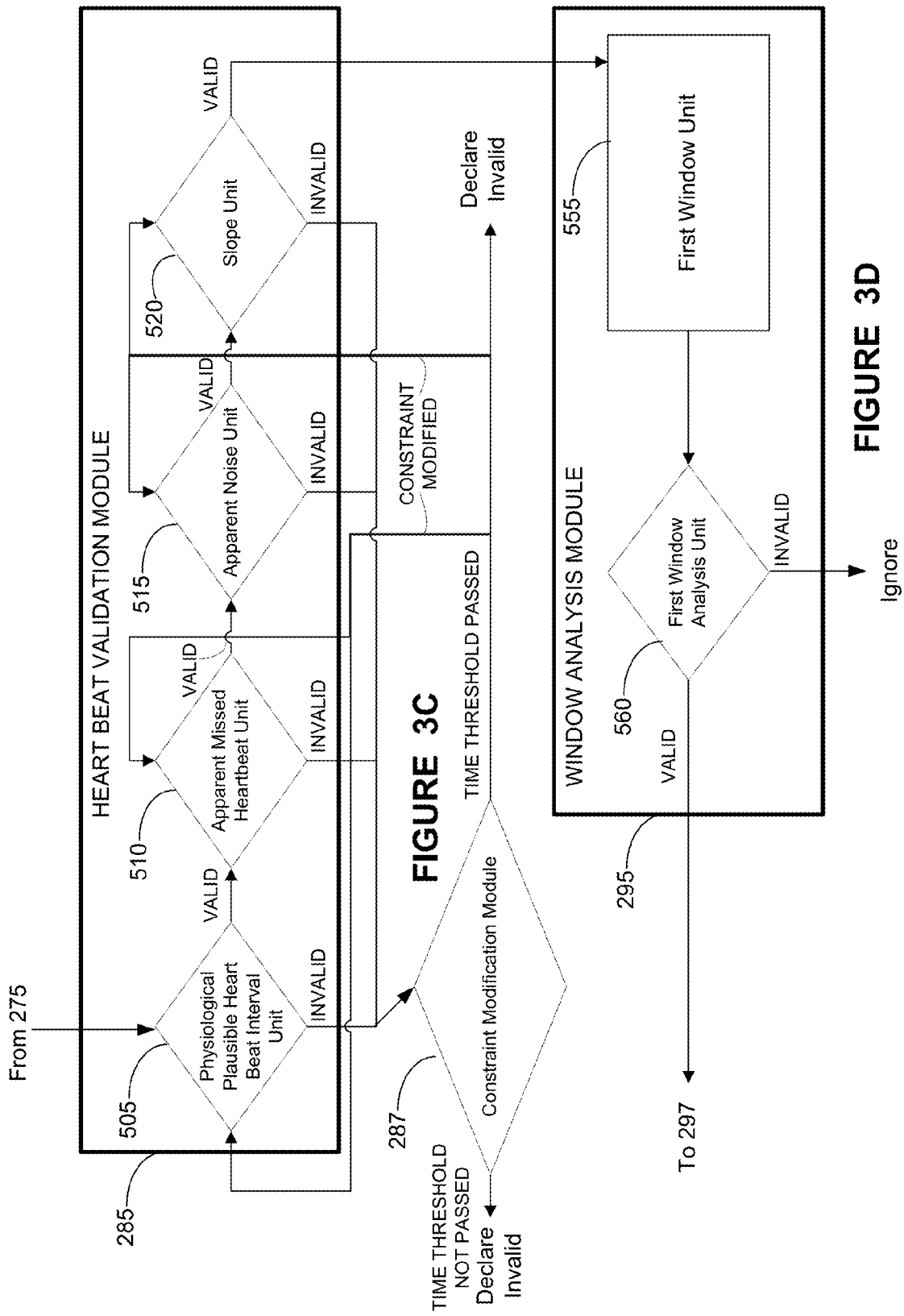

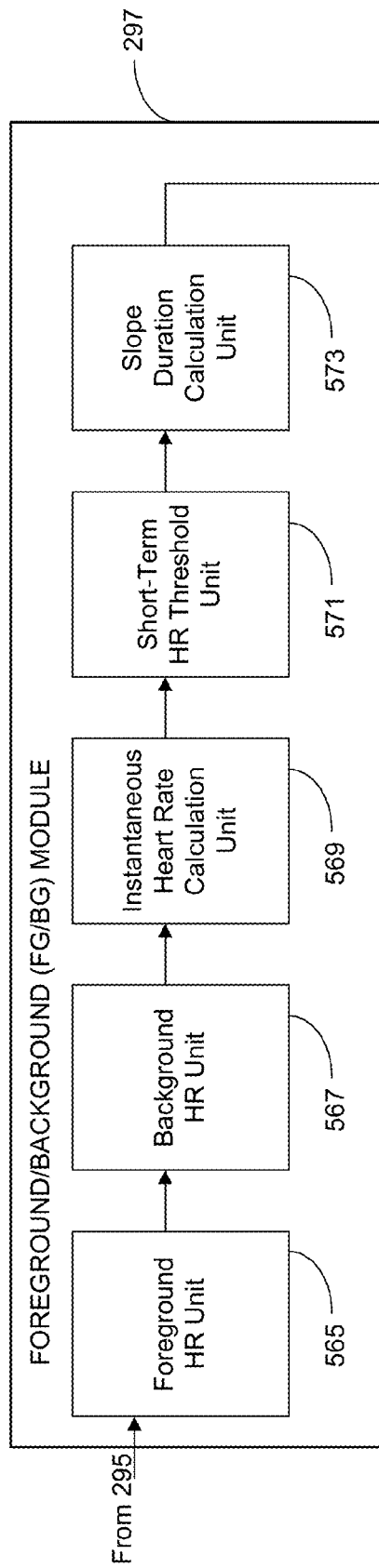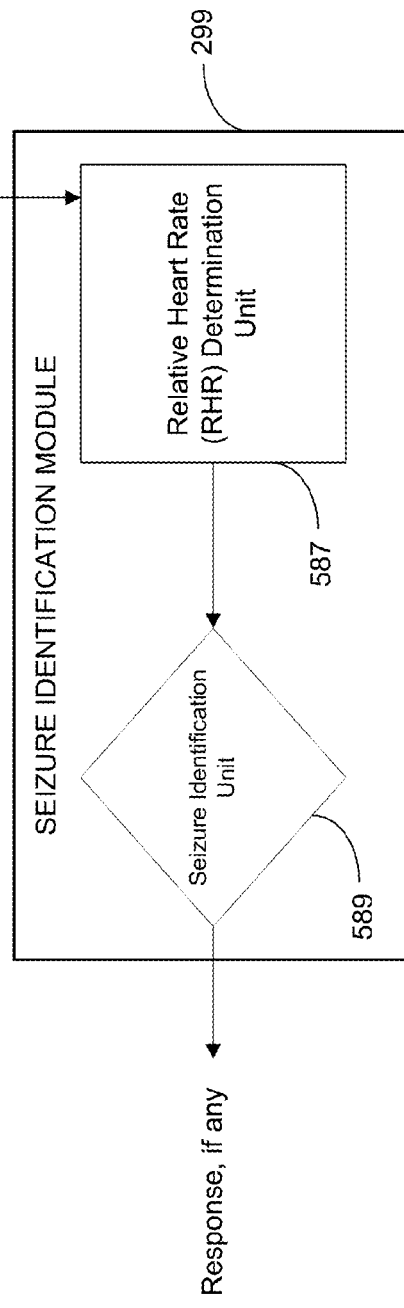
FIGURE 3E
FIGURE 3F

_US 9,750,448 B2_

METHOD, APPARATUS AND SYSTEM FOR VALIDATING AND QUANTIFYING CARDIAC BEAT DATA QUALITY

CROSS-REFERENCE TO RELATED APPLICATIONS

This application is a continuation of co-pending application Ser. No. 12/771,727 filed Apr. 30, 2010, which is a continuation-in-part of U.S. patent application Ser. No. 12/770,562, filed Apr. 29, 2010, now U.S. Pat. No. 8,562,536, which issued on Oct. 22, 2013. Both Ser. Nos. 12/771,727 and 12/770,562 are hereby incorporated by reference herein.

1. FIELD OF THE INVENTION

This invention relates to medical device systems and methods capable of detecting and, in some embodiments, treating an occurring, impending, or recently occurred seizure.

2. DESCRIPTION OF THE RELATED ART

Of the approximately 60 million people worldwide affected with epilepsy, roughly 23 million people suffer from epilepsy resistant to multiple medications. In the USA alone, the annual cost of epilepsy care is USD 12 billion (in 1995 dollars), most of which is attributable to subjects with pharmaco-resistant seizures. Pharmaco-resistant seizures are associated with an increase mortality and morbidity (compared to the general population and to epileptics whose seizures are controlled by medications) and with markedly degraded quality of life for patients. Seizures may impair motor control, responsiveness to a wide class of stimuli, and other cognitive functions. The sudden onset of a patient's impairment of motor control, responsiveness, and other cognitive functions precludes the performance of necessary and even simple daily life tasks such as driving a vehicle, cooking, or operating machinery, as well as more complex tasks such as acquiring knowledge and socializing.

Therapies using electrical currents or fields to provide a therapy to a patient (electrotherapy) are beneficial for certain neurological disorders, such as epilepsy. Implantable medical devices have been effectively used to deliver therapeutic electrical stimulation to various portions of the human body (e.g., the vagus nerve) for treating epilepsy. As used herein, "stimulation," "neurostimulation," "stimulation signal," "therapeutic signal," or "neurostimulation signal" refers to the direct or indirect application of an electrical, mechanical, magnetic, electro-magnetic, photonic, acoustic, cognitive, and/or chemical signal to an organ or a neural structure in the patient's body. The signal is an exogenous signal that is distinct from the endogenous electro-chemical activity inherent to the patient's body and also from that found in the environment. In other words, the stimulation signal (whether electrical, mechanical, magnetic, electro-magnetic, photonic, acoustic, cognitive, and/or chemical in nature) applied to a cranial nerve or to other nervous tissue structure in the present invention is a signal applied from a medical device, e.g., a neurostimulator.

A "therapeutic signal" refers to a stimulation signal delivered to a patient's body with the intent of treating a medical condition through a suppressing (blocking) or modulating effect to neural tissue. The effect of a stimulation signal on neuronal activity may be suppressing or modulating; however, for simplicity, the terms "stimulating", suppressing, and modulating, and variants thereof, are sometimes used interchangeably herein. In general, however, the delivery of an exogenous signal itself refers to "stimulation" of an organ or a neural structure, while the effects of that signal, if any, on the electrical activity of the neural structure are properly referred to as suppression or modulation.

Depending upon myriad factors such as the history (recent and distant) of the nervous system, stimulation parameters and time of day, to name a few, the effects of stimulation upon the neural tissue may be excitatory or inhibitory, facilitatory or disfacilitatory and may suppress, enhance, or leave unaltered neuronal activity. For example, the suppressing effect of a stimulation signal on neural tissue would manifest as the blockage of abnormal activity (e.g., epileptic seizures) see Osorio et al., Ann Neurol 2005; Osorio & Frei IJNS 2009) The mechanisms thorough which this suppressing effect takes place are described in the foregoing articles. Suppression of abnormal neural activity is generally a threshold or suprathreshold process and the temporal scale over which it occurs is usually in the order of tens or hundreds of milliseconds. Modulation of abnormal or undesirable neural activity is typically a "sub-threshold" process in the spatio-temporal domain that may summate and result under certain conditions, in threshold or suprathreshold neural events. The temporal scale of modulation is usually longer than that of suppression, encompassing seconds to hours, even months. In addition to inhibition or dysfacilitation, modification of neural activity (wave annihilation) may be exerted through collision with identical, similar or dissimilar waves, a concept borrowed from wave mechanics, or through phase resetting (Winfree).

In some cases, electrotherapy may be provided by implanting an electrical device, i.e., an implantable medical device (IMD), inside a patient's body for stimulation of a nervous tissue, such as a cranial nerve. Generally, electrotherapy signals that suppress or modulate neural activity are delivered by the IMD via one or more leads. When applicable, the leads generally terminate at their distal ends in one or more electrodes, and the electrodes, in turn, are coupled to a target tissue in the patient's body. For example, a number of electrodes may be attached to various points of a nerve or other tissue inside a human body for delivery of a neurostimulation signal.

While contingent (also referred to as "closed-loop," "active," or "feedback" stimulation (i.e., electrotherapy applied in response to sensed information, such as heart rate)) stimulation schemes have been proposed, non-contingent, programmed periodic stimulation is the prevailing modality. For example, vagus nerve stimulation for the treatment of epilepsy usually involves a series of grouped electrical pulses defined by an "on-time" (such as 30 sec) and an "off-time" (such as 5 min). This type of stimulation is also referred to as "open-loop," "passive," or "non-feedback" stimulation. Each sequence of pulses during an on-time may be referred to as a "pulse burst." The burst is followed by the off-time period in which no signals are applied to the nerve. During the on-time, electrical pulses of a defined electrical current (e.g., 0.5-3.5 milliamps) and pulse width (e.g., 0.25-1.0 milliseconds) are delivered at a defined frequency (e.g., 20-30 Hz) for a certain duration (e.g., 10-60 seconds). The on-time and off-time parameters together define a duty cycle, which is the ratio of the on-time to the sum of the on-time and off-time, and which describes the fraction of time that the electrical signal is applied to the nerve.

In VNS, the on-time and off-time may be programmed to define an intermittent pattern in which a repeating series of electrical pulse bursts are generated and applied to a cranial nerve such as the vagus nerve. The off-time is provided to minimize adverse effects and conserve power. If the off-time is set at zero, the electrical signal in conventional VNS may provide continuous stimulation to the vagus nerve. Alternatively, the off time may be as long as one day or more, in which case the pulse bursts are provided only once per day or at even longer intervals. Typically, however, the ratio of "off-time" to "on-time" may range from about 0.5 to about 10.

In addition to the on-time and off-time, the other parameters defining the electrical signal in VNS may be programmed over a range of values. The pulse width for the pulses in a pulse burst of conventional VNS may be set to a value not greater than about 1 msec, such as about 250-500 μsec, and the number of pulses in a pulse burst is typically set by programming a frequency in a range of about 20-300 Hz (i.e., 20 pulses per second to 300 pulses per second). A non-uniform frequency may also be used. Frequency may be altered during a pulse burst by either a frequency sweep from a low frequency to a high frequency, or vice versa. Alternatively, the timing between adjacent individual signals within a burst may be randomly changed such that two adjacent signals may be generated at any frequency within a range of frequencies.

Although neurostimulation has proven effective in the treatment of a number of medical conditions, it would be desirable to further enhance and optimize neurostimulation-based therapy for this purpose. For example, it may be desirable to detect an occurring or impending seizure. Such detection may be useful in triggering a therapy, monitoring the course of a patient's disease, or the progress of his or her treatment thereof. Alternatively or in addition, such detection may be useful in warning the patient of an impending seizure or alerting the patient, a physician, a caregiver, or a suitably programmed computer in order for that person or computer program to take action intended to reduce the likelihood, duration, or severity of the seizure or impending seizure, or to facilitate further medical treatment or intervention for the patient. In particular, detection of an occurring or impending seizure enables the use of contingent neurostimulation. The state of the art does not provide an efficient and effective means for performing such detection and/or warning. Conventional VNS stimulation as described above does not detect occurring or impending seizures.

SUMMARY OF THE INVENTION

In one embodiment, the present invention provides a method for quantifying the quality of a fiducial time marker for a candidate heart beat. In one embodiment, the method comprises obtaining a fiducial time marker for a candidate heart beat in a first time series of candidate heart beats; setting a beat quality index for said candidate heart beat to a first value; testing said candidate heart beat with a first beat validity test; setting said beat quality index to at least a second value indicative of whether said at least one beat validity test was passed; testing said candidate heart beat with at least a second heart beat validity test; setting said beat quality index to at least a third value indicative of whether said at least a second heart beat validity test was passed; and performing at least one responsive action based upon the value of said beat quality index, the responsive action selected from the group consisting of issuing a detection for an epileptic seizure event;

delivering therapy to the patient to treat a medical condition;

warning at least one of a caregiver, the patient, or a physician; and logging said beat quality index to a memory.

In one embodiment, the present invention provides a method for quantifying the quality of a candidate heart beat. In one embodiment, the method comprises receiving a reference time marker for a signal portion representative of a candidate heart beat; determining a first quality criterion for validating said candidate heart beat; testing said candidate heart beat with a first beat validity test using at least said first quality criterion; determining a second quality criterion for validating said candidate heart beat; testing said candidate heart beat with a second beat validity test using at least said second quality criterion; associating a beat quality certification to said candidate heart beat based on said first and second beat validity tests; and performing at least one responsive action based upon the value of said beat quality index, the responsive action selected from the group consisting of issuing a detection for an epileptic seizure event;

delivering therapy to the patient to treat a medical condition;

warning at least one of a caregiver, the patient, or a physician; and logging said beat quality index to a memory. In one embodiment, the first and second quality criteria comprise first and second thresholds.

In another aspect of the present invention, a method for determining a time of beat sequence of the patient's heart is provided. The method comprises obtaining a time series of fiducial time markers for candidate heart beats; identifying valid heart beats from said candidate heart beats by subjecting a plurality of said candidate heart beats to at least one beat validity test, said at least one beat validity test comprising at least one interbeat interval test applied to a candidate heart beat interval derived from a candidate heart beat and at least one preceding heart beat; accepting as valid heart beats the candidate heart beats that pass said at least one beat validity test, wherein a constraint defining said pass is modified after the most recent prior valid heart beat that is greater than a constraint modification time threshold; and performing at least one responsive action based upon at least one said valid heart beat, the responsive action selected from the group consisting of issuing a detection for an epileptic seizure event;

delivering a neurostimulation therapy to the patient to treat medical condition;

warning at least one of a caregiver, the patient, or a physician; and logging said modified constraint to a memory.

In yet another aspect of the present invention, a computer readable program storage device is provided that is encoded with instructions that, when executed by a computer, perform a method described above.

In one embodiment, a medical device is provided comprising a computer readable program storage device as described above.

BRIEF DESCRIPTION OF THE DRAWINGS

The invention may be understood by reference to the following description taken in conjunction with the accompanying drawings, in which like reference numerals identify like elements, and in which:

FIG. 3C is a stylized block diagram of a heart beat validation module of a medical device, in accordance with one illustrative embodiment of the present invention;

FIG. 3D is a stylized block diagram of a window analysis module of a medical device, in accordance with one illustrative embodiment of the present invention;

FIG. 3E is a stylized block diagram of a foreground/background module of a medical device, in accordance with one illustrative embodiment of the present invention;

FIG. 3F is a stylized block diagram of a seizure detection module of a medical device, in accordance with one illustrative embodiment of the present invention;

Figure 1A:
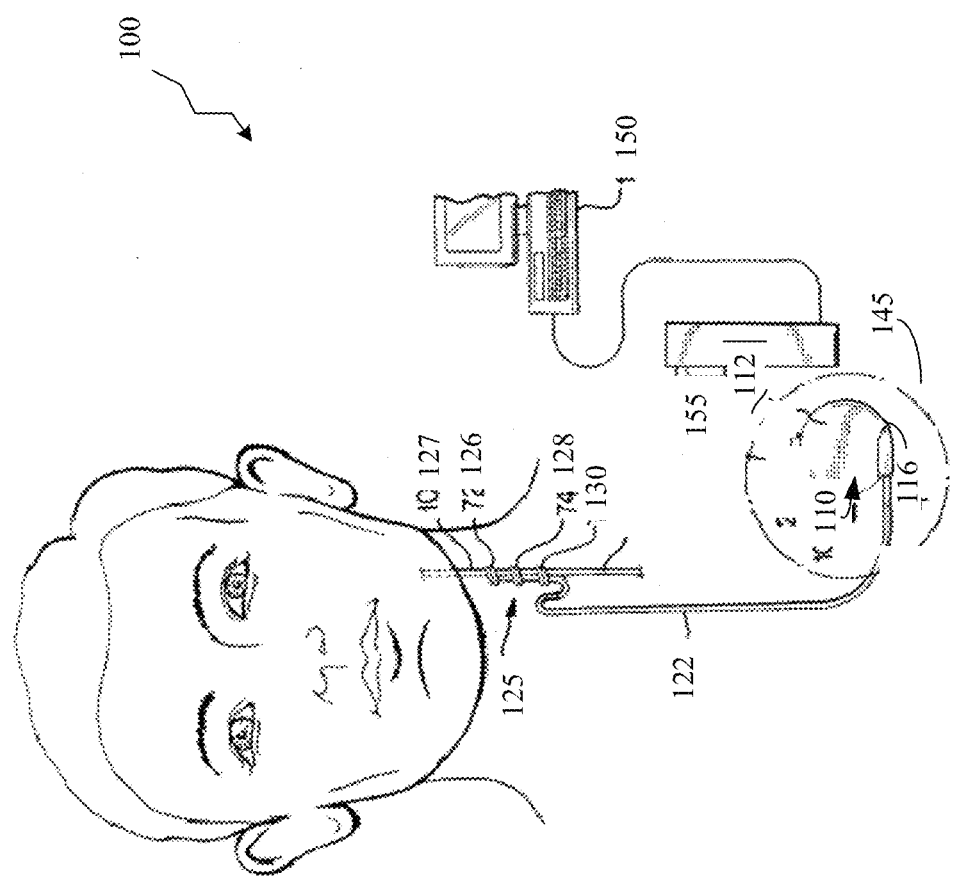
FIG. 1A provides a stylized diagram of a medical device implanted into a patient's body for providing a therapeutic electrical signal to a neural structure of the patient's body, in accordance with one illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

This document does not intend to distinguish between components that differ in name but not function. In the following discussion and in the claims, the terms "including" and "includes" are used in an open-ended fashion, and thus should be interpreted to mean "including, but not limited to." Also, the term "couple" or "couples" is intended to mean either a direct or an indirect electrical connection. "Direct contact," "direct attachment," or providing a "direct coupling" indicates that a surface of a first element contacts the surface of a second element with no substantial attenuating medium there between. The presence of small quantities of substances, such as bodily fluids, that do not substantially attenuate electrical connections does not vitiate direct contact. The word "or" is used in the inclusive sense (i.e., "and/or") unless a specific use to the contrary is explicitly stated.

The term "electrode" or "electrodes" described herein may refer to one or more stimulation electrodes (i.e., electrodes for delivering a therapeutic signal generated by an IMD to a tissue), sensing electrodes (i.e., electrodes for sensing a physiological indication of a state of a patient's body), and/or electrodes that are capable of delivering a therapeutic signal, as well as performing a sensing function.

The term "beat validity test" (BVT) is intended to describe a test or evaluation of a sensor signal (or portion thereof) indicative of a candidate heart beat to determine whether the candidate beat is a true beat that is actually indicative of a heart beat of the patient, or is instead a spurious signal that does not actually indicate a heart beat of the patient. The sensor signal may be, for example, a portion of an EKG signal corresponding to an R-wave peak, another electrical signal indicative of a heart beat, a phonocardiogram (PKG) signal, or another signal used for sensing heart beats. In some embodiments, the signal may be pre-processed and/or filtered to remove extraneous noise before being subjected to a BVT.

BVTs according to some embodiments of the invention operate on a single candidate beat or a single instant of time (e.g., a timestamp for a single candidate beat). It will be appreciated, however, that a BVT (which may be, for example, an interbeat interval test or a window test) may involve additional beats near the candidate beat. Thus, a BVT that is used to score (or update a beat quality index for) a single beat may incorporate prior information (such as timestamps for prior heart beats or candidate heart beats. While the term "window test" refers to a test that incorporates information beyond a single timestamp and involves candidate heart beats within an interval of time, the window test may be used to score a single heart beat (such as the most recent candidate beat in the window) or multiple beats.

The term "beat quality index" (BQI) is a measure of the results of one or more BVTs applied to a candidate heart beat or, in some instances, a plurality of candidate heart beats such as a BQI for a window of time. A time series of BQIs for individual heart beats may be developed to indicate periods in which sensed heart beat data is highly reliable (i.e., instances in which many individual heart beats in a series have high BQI scores) or is poor (i.e., when many beats in a stream show relatively low BQI scores indicative of having failed one or more BVTs). BQI scores may also be developed for particular periods or windows of interest, such as a period encompassing some time prior, during and/or after an epileptic seizure event, discussed more fully hereinafter. In some embodiments, the BQI may comprise a single value. In alternative embodiments, the BQI may comprise a matrix of multiple values.

In one embodiment, the present invention provides a method of detecting a seizure event based upon heart activity, such as a time of beat sequence of the patient's heart beat. The seizure event can be, for example, at least one of an unstable brain state, a brain state indicative of an elevated probability of a seizure, a brain state indicative of an impending seizure, or a seizure, among others.

In one embodiment, the present invention comprises a method for quantifying the quality of a candidate heart beat in a time series of candidate heart beats. The method involves obtaining fiducial time markers for candidate heart beats in a time series of such beats, testing at least some of the beats with a plurality of beat quality tests, and setting a beat quality index parameter to a value indicative of whether the candidate beat passes the beat quality tests. In a particular embodiment, the method comprises obtaining a fiducial time marker for a candidate heart beat in a first time series of candidate heart beats; setting a beat quality index for the candidate heart beat to a first value; testing the candidate beat with a first beat validity test; setting the beat quality index to a second value indicative of whether the candidate beat passed the first beat validity test; testing the candidate heart beat with a second beat validity test; setting the beat quality index to a third value indicative of whether the candidate beat passed or failed the second beat validity test; and performing at least one action in response to setting the beat quality index to the third value. Responsive actions may include storing the BQI value in a log; sending a signal indicative of the BQI value; providing a warning of a low BQI value, initiating a therapy for a medical condition, notifying a third party of the BQI value (such as a caregiver, physician, the patient, or EMS service); and initiating a seizure severity index scoring routine.

In one embodiment of the present invention, the method comprises generating a time series of fiducial time markers for candidate heart beats; identifying valid beats from the candidate heart beats by at least one beat validity test; and determining a beat quality index for a plurality of candidate heart beats in said time series based on said at least one beat validity test In some embodiments, the at least one beat validity test comprises a test of an interbeat interval including a candidate heart beat. In some embodiments, the at least one beat validity test comprises a window test including the candidate heart beat.

In one embodiment, a First Module may be capable of receiving a signal relating to a heart activity and deciphering at least a portion of the signal for identifying one or more candidate heart beats. The First Module may be capable of identifying wholly or in part, the quality of one or more candidate heart beats. In one embodiment, the step of identifying valid beats from candidate heart beats may be performed in the First Module that also performs quality analysis on the candidate heart beats to distinguish physiologically plausible from physiologically implausible candidate heart beats. In a further embodiment, the First Module can quantify, wholly or in part, the quality of one or more candidate heart beats.

In one embodiment, a Second Module is capable of an independent evaluation of the signal relating to a heart activity, and/or a further refinement of the process of identifying candidate heart beat or validating a candidate heart beat as a valid heart beat. The evaluation of the signal relating to a heart activity may include quantifying wholly, or in part, the quality of one or more candidate heart beats. In a particular embodiment, the Second Module is capable of updating a BQI index score to reflect the results of a window test. In one embodiment, the step of identifying valid beats suitable for seizure detection may be performed in the Second Module by performing a dispersion analysis on a window formed to test each of the valid beats to ensure that the valid beats are acceptable for use in detecting epileptic seizure events. In a further embodiment, the Second Module can quantify wholly or in part, the quality of one or more candidate heart beats.

In one embodiment, a Third Module is capable of detecting an epileptic seizure event based upon one or more indications provided by the signal relating to a heart activity. In one embodiment, detection of an epileptic seizure event may be performed by the Third Module that detects an epileptic seizure event based upon a ratio of a measure of central tendency of valid beats in a first, relatively short window and a measure of central tendency of valid beats in a second window longer than the first window. In other embodiments, a Third Module may alternatively or in addition detect an epileptic seizure event based on other parameters calculated from valid beats.

First Module

The first module is capable of receiving a heart signal representative or relating to the heart activity of a patient. The first module is capable of processing the heart signal and deriving information such as probable heart beats from the heart signal. These probable or candidate heart beats may be tested with one or more beat validity tests to determine how likely they are to be a true heart beat, as opposed to a spurious or false heart beat. The results of such tests may be quantified (e.g., the quality of the candidate heart beats, the validity of the heart beats, etc.) by the first module as a beat quality index. Heart beats deemed valid may be identified in the method by subjecting a plurality of candidate beats to at least one beat validity test in which at least one candidate beat interval is derived from a candidate heart beat and at least one preceding heart beat, and subjected to a test to determine its validity. In one embodiment the validity test comprises a test to determine if the candidate beat interval is physiologically plausible. Regardless of which test is used, candidate beats that pass the at least one beat validity test are accepted as valid.

In one embodiment of the invention, all candidate heart beats may be considered as valid beats. For extremely reliable sensing elements, or for embodiments with low noise (e.g., intracardiac electrodes such as those used in pacemakers), candidate heart beats may be so reliable that beat validity testing may be omitted.

Identifying valid beats from candidate heart beats may involve declaring invalid certain candidate heart beats if the candidate beat interval relating to those beats is not physiologically valid or plausible. In one embodiment, being physiologically invalid may mean that a candidate beat, in conjunction with a prior heart beat, indicates a heart rate (HR) that is outside of physiologically plausible upper and lower HR limits. In a particular embodiment, candidate heart beats are discarded if the candidate beat and a prior beat correspond to a heart rate that is below 35 beats per minute (BPM) or above 180 BPM. In other embodiments, candidate beats may be discarded for other reasons including: being so long as to suggest sinus arrest (e.g., a missed heart beat), being so short as to appear to be due to noise, having a slope (in conjunction with a prior heart beat) that is too large to be physiologically plausible (in other words, the candidate heart beat would mean that the heart rate has experienced a sudden acceleration or deceleration that is physiologically implausible), or two or more of the foregoing.

Other embodiments of the present application may provide for utilizing one or more of the beat validity tests described herein to perform additional functions, such as quantifying the robustness and/or reliability of a candidate heart beat or a fiducial or reference time marker therefor. This may involve setting a beat quality index associated with a candidate heart beat to a value based on whether the candidate heart beat passes the one or more beat validity tests. In one embodiment, the beat quality index may be set to first value, such as an integer, and set to another value based upon the outcome of the one or more beat validity tests.

A beat quality index may be determined for each candidate heart beat in a first time series of candidate heart beats to provide a second time series of candidate beat quality indices. The second time series of beat quality indices may indicate periods of high and low robustness and/or reliability for candidate heart beats.

In one embodiment, the beat validity tests used to determine the beat quality index for a candidate heart beat may be manually selected by a physician. In another embodiment, a library of BVTs may be maintained and used to determine which BVTs to use for a particular patient to optimize accuracy of beat detections. For example, BVTs applied to individual beats, interbeat intervals, and/or windows may be used to analyze historical data for a particular patient or group of patients. One or more BVTs for use in determining BQIs may be determined automatically by testing historical data with the BVTs from the library over a baseline analysis period, for example one week to six months. An analysis program may determine, from historical time markers of candidate heart beats, which BVTs provide more reliable indications of true beats and the lowest indication of spurious beats, and these BVTs may be used to determine BQI values and seizure events. The BVTs may be periodically re-evaluated and changed to maintain maximum efficiency in beat identification. The BVTs may be selected by a physician or selected automatically, based upon analysis of the patient's heart beats and/or BQIs.

The library of BVTs may also or alternatively include one or more window tests, as described herein.

Any BVTs referred to herein or in U.S. Ser. No. 12/770, 562, incorporated herein by reference, may be used. In one embodiment, the BVT makes use of a match filter derived from one or more previously observed patterns of candidate beats and applied to a window of cardiac data.

From the data stream of individual beat quality indices, window beat quality indices may also be determined by providing a statistical measure of central tendency for the individual beat quality index values of the candidate beats in the window. In one embodiment, moving windows may be determined for each candidate beat that extends from the candidate beat to a desired period prior to the beat, such as 5 minutes to 24 hours. A window beat quality index may be determined as a statistical measure of central tendency, such the $50^{th}$ percentile in a uniform distribution percentile tracking filter, for the candidate beats in the window, for example a five minute moving window. When the value of the window beat quality index is below a threshold value for window beat quality, the value of the beat quality index may be logged and used to indicate that a period of low data quality has occurred.

As used herein, the term "statistical measure of central tendency" refers to any statistical measure of a location within a distribution, and not necessarily a mean, median, or $50^{th}$ percentile value. For example, in one embodiment, the statistical measure of central tendency is the $30^{th}$ percentile in a uniform distribution percentile tracking filter Beat quality indices for particular windows of interest may also be created, for example, for a window based upon an indication of an epileptic seizure event as determined from one or more cardiac parameters. The window based upon an indication of an epileptic seizure event may be termed a "seizure window." The window may begin at any desired time before or after the indication of a seizure, and may have a defined duration. In one embodiment, the time window may begin at a time between 30 minutes before the seizure and 30 minutes after the seizure, and the window may have a duration of from about 5 minutes to about 2 hours. A seizure window beat quality index may be determined from a statistical measure of central tendency from the individual beat quality indices for the candidate heart beats in the seizure window.

In one embodiment the beat quality index may be incremented by a particular value (which may be unique for each beat validity test, thus allowing certain tests to be weighted more than other tests) based upon the outcome of the test. In still another embodiment, a unique value may be provided based upon the outcome of each of the beat validity tests. For example, the BQI may comprise a binary number having a number of digits equal to the number of beat validity tests. For each test that is failed a 0 may be entered for the digit associated with that test, and a 1 may be entered for each test that is passed. Thus, a unique beat quality index may be provided for each candidate heart beat that indicates for each BVT whether the test was passed or not.

Alternatively or in addition, in a further embodiment, valid heart beats can be identified from candidate heart beats by subjecting a plurality of candidate beats to at least one beat validity test as referred to above, and accepting as valid beats the candidate beats that pass said at least one beat validity test, wherein a constraint defining said pass is modified at one or more times after the most recent prior valid heart beat that is greater than a constraint modification time threshold.

In another embodiment, a constraint modification time threshold can be used in conjunction with one or more beat validity tests. In this embodiment, even if a candidate heart beat passes the at least one beat validity test after a constraint is modified, the value of the beat quality may, but need not, be reset to a value indicative of a pass. In other words, beat quality can be defined independently of whether a beat was found valid, valid and suitable for seizure detection, or neither.

The constraint modification time threshold may be a constant, such as 3 sec, 5 sec, 7 sec, 10 sec, 30 sec, or 60 sec, among even shorter or longer times. In another embodiment, the constraint modification time threshold is set at an initial value when a valid beat is accepted and decreases with each consecutive candidate beat not accepted as valid. In other words, the constraint modification time threshold may, but need not, be adaptive. For example, the initial value may be one of those stated above, and the constraint modification time threshold may be decreased linearly (e.g., n sec per consecutive candidate beat not accepted as valid), exponentially (e.g., by $threshold_{new}=k*threshold_{old}$, where k<1), or by other formulas. The constraint modification time threshold may also be adaptive based on observations of the patient, i.e., set to longer or shorter values at different times of day, week, month, or year; different states of the patient's medical condition; etc.

"Constraint modification" encompasses relaxation of the constraint, tightening of the constraint, other changes which simply change the set of candidates that may be considered passing, without necessarily relaxing or tightening, and two or more thereof. Constraint relaxation refers to the alteration of one or more parameters used to define the constraint in a way that makes the constraint/validity test more likely to be satisfied, i.e., enlarging the set of candidate beats which would be considered valid. Similarly, constraint tightening refers to the alteration of one or more parameters used to define the constraint in a way that makes the constraint/validity test less likely to be satisfied. As an illustrative example, in one embodiment, the beat validity test is a test whether the instantaneous heart rate (IHR) calculated from a candidate heart beat and the most recent prior beat falls within a range bounded by minimum IHR (m)=35 bpm and maximum IHR (M)=180 bpm. Altering the parameters to m=20 bpm, M=220 bpm is considered constraint relaxation (by about 38%, i.e., (220−20)/(180−35)). Altering the parameters to m=40 bpm, M=180 bpm is tightening the constraint by about 3%. Altering the parameters to m=50 bpm, M=195 bpm is constraint modification but not necessarily relaxation or tightening.

In one embodiment, the constraint is modified by relaxing the constraint by from about 1% to about 50%. By this is meant raising or lowering the constraint by from about 1% to about 50% above or below its initial value. In another embodiment, the constraint is modified by relaxing the constraint by greater than about 50%, such as from about 50% to infinity. As will be apparent to the person of ordinary skill in the art having the benefit of the present disclosure, relaxing a constraint to infinity will result in the constraint always being met, i.e., the candidate heart beat always passing the beat validity test. In yet another embodiment, the constraint is modified by tightening said constraint by from about 1% to about 50%, or even greater than about 50%, such as from about 50% to infinity. As will be apparent to the person of ordinary skill in the art having the benefit of the present disclosure, tightening a constraint to infinity will result in the constraint never being met, i.e., the candidate heart beat never passing the beat validity test.

The constraint may be modified once or at a plurality of times after the constraint modification time threshold is passed. Regardless of how often the constraints is modified, the constraint may be modified according to a step function, a linear function, or a non-linear function over a range of times after the constraint modification time threshold is passed. Regardless of the function defining constraint modification, the constraint may be modified to no more or less than a finite maximum or minimum value, respectively, or the constraint may be modified up to infinity or negative infinity.

For a particular example of constraint relaxation, in one embodiment, a first beat validity test requires a candidate heart beat to correspond to an instantaneous heart rate (IHR) of between 35 bpm (m) and 180 bpm (M) to be considered valid. In this example, these limits [m,M] are time-varying and set to $$[m,M]=\min(275,\max(20,[35,180]+[-2,5]*\max(0,(\text{time\_since\_last\_valid\_beat}-5)))).$$

Figure 8:
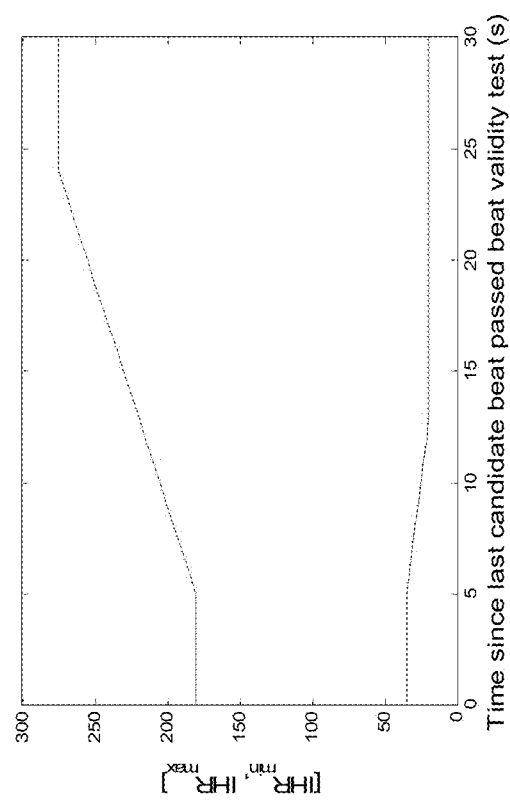
FIG. 8 graphically depicts a constraint relaxation, according to one embodiment of the present invention.

This formula keeps the original constraint (m=35, M=180) in place for 5 seconds, then lowers the bottom limit, m, by 2 bpm/sec and raises the upper limit, M, by 5 bpm/sec, but never lets the lower limit fall below 20 bpm or the upper limit exceed 275 bpm. For example, after 6 s without a valid beat detection, the test would be whether the candidate beat corresponds to an IHR between 33 bpm and 185 bpm, after 7 s the test would be whether the candidate beat corresponds to an IHR between 31 bpm and 190 bpm, etc. (FIG. 8 depicts the formula's output graphically). In other words, this example relaxes the constraint according to a linear function up to finite maximum and minimum values.

For a particular example of constraint tightening, it may be learned from a particular subject that his or her heart rate is always between 50 bpm and 170 bpm (even during seizures) unless the signal encounters movement artifacts (e.g., during exercise). This could be learned over time so that after a period of monitoring and logging this information, the original (generic) [35, 180] bpm constraints could be tightened for this individual to [50,170] bpm, which would perform better for this subject. Tests could be tightened during detected artifacts not associated with seizures to avoid false positive detections, or relaxed during artifact-free periods to track wider ranges in cardiac dynamics (such as higher or lower IHRs than allowed through the generic constraint settings).

Second Module

In one embodiment, the second module is capable of evaluating heart beat information derived from the heart signal. In another embodiment, the second module is operatively coupled with the first module and is capable of further processing of heart beat information from the first module. In one embodiment, the second module may independently (with reference to the operation of the first module) analyze candidate heart beat to quantify beat quality and/or validate candidate heart beats. In another embodiment, the second module is capable of performing further quantification of beat quality or validation of heart beats performed by the first module.

In one embodiment, from the valid beats identified by the beat interval test, valid beats suitable for seizure detection may be identified by further testing performed by the second module. The testing may involve forming a first window (which may be a time window or a number-of-beats window) for each valid beat that includes both a first valid beat and at least one preceding heart beat. In one embodiment, the window is a backward-looking time window bounded at one end by the first valid beat. The first window is tested with at least one window test, and if the first window passes the at least one window test, the first valid beat from the window is accepted as suitable for seizure detection.

Any window referred to herein may comprise a time window or a number-of-beats window. The window may be a simple window (of finite length and with equal weighting for each time unit or beat unit in the window). In one embodiment, any window referred to herein may also be of infinite length, utilizing any non-negative function with unit area under the curve as a time-weight. In one embodiment, any window referred to herein may be an exponential moving window with time constant T and corresponding timescale 1/T, which preferably weights more recent information over "exponentially forgotten" prior information. The time constant determines how rapidly information is forgotten by controlling the decay rate of the exponential time weight.

Exponential moving windows can be easily used and readily implemented in analog. More detail on the types of windows usable according to the present application can be found in U.S. Pat. Nos. 6,768,969; 6,904,390; and 7,188,053, the disclosures of which are hereby incorporated herein by reference.

In some embodiments of the invention, it may be unnecessary to distinguish between valid beats and valid beats suitable for seizure detection. In such embodiments, all valid beats may be considered as suitable for seizure detection. Where this is the case, formation of a first window, and performing dispersion and/or other tests on the first window, may be omitted.

Identifying valid beats that are suitable for seizure detection may involve forming a time-based or number-of-beats first window from a first valid beat and at least one preceding heart beat, testing the first window, and accepting the first valid beat as suitable for seizure detection if the first window passes the test. The first window may be, as a nonlimiting example, a 5 second window bounded on the present side by the first valid beat (i.e., the window extends 5 seconds back in time from the first valid beat). Such a window may comprise, for example, from 2-15 beats in the window depending upon the patient's heart rate. Testing the first window may involve applying one or more dispersion tests to the beats in the window. Such tests allow the first valid beat to be reviewed in the context of neighboring valid beats, and thus recent cardiac activity, to determine its suitability for use in seizure detection calculations. In one embodiment, the dispersion test may involve a short-term heart rate variability (HRV) measure of the beats in the window. In a particular embodiment, the HRV may be calculated as the mean squared error of a least-squares linear fit of the heart beats in the first window. Other HRV tests may also—or alternatively—be used. Additional dispersion tests such as upper and/or lower limits for the number of beats in the window may also be used in some embodiments.

In another embodiment, valid heart beats are subjected to one or more homogeneity tests to ensure that the candidate heart beat data is composed exclusively of cardiac data, and to eliminate data that is not of cardiac origin. In one embodiment, the data in the first window may be tested to identify data with excessive variation from a central tendency measure such as a median, mean, or an adaptive uniform distribution-based Percentile Tracking Filter, discussed more fully hereinafter. In a specific embodiment, the homogeneity test comprises (i) determining the median of a plurality of data points (e.g., interpulse intervals) in the window; (ii) subtracting the median from each data point; (iii) determine the number of data points above and below the median (i.e., persistence of positive or negative values; (iv) compare the persistence of positive and negative values to at least one homogeneity threshold; and (v) reject data points exceeding the homogeneity threshold. Homogeneity thresholds may be identified by a mathematical function, or by significance tables stored in a memory.

In one embodiment, the result(s) of the at least one window test can be used to quantify the quality of a candidate heart beat or a fiducial time marker for a candidate heart beat. This may involve setting (e.g., by incrementing a counter) a beat quality index associated with a candidate heart beat.

Regardless of whether quantification of beat quality is performed by the first module the second module, or both, in one embodiment, the invention comprises performing a responsive action based upon the value of the beat quality index. The responsive action may be selected from the group consisting of:

indicating the occurrence of an epileptic seizure event;
delivering a neurostimulation therapy to the patient to treat a medical condition;
warning at least one of a caregiver, the patient, or a physician; and
logging the beat quality index to a memory.

In one embodiment, delivering a neurostimulation therapy may comprise initiating a programmed neurostimulation therapy. In another embodiment, providing a neurostimulation therapy may involve modifying a programmed neurostimulation therapy to obtain a second neurostimulation therapy and applying the second neurostimulation therapy to a target neural structure. "Modifying a neurostimulation" or similar language refers to one of a) changing a at least one parameter defining an electrical stimulation signal applied to a target body tissue of a patient, b) switching from non-responsive or open-loop to contingent or closed-loop stimulation, or vice versa. In one embodiment, the stimulation comprises one or more electrical signals administered to a neural structure of a patient.

The "parameters derivable from said one or more of said candidate heart beats" include valid beats, valid beats suitable for seizure detection, interbeat intervals derived from candidate heart beats, valid beats, or valid beats suitable for seizure detection by the formula: interbeat interval (in seconds)=heart rate (in BPM)/60), heart rate, and heart rate variability (HRV), among others. The "parameters derivable from said beat quality index" include a mean, median, and other measures of central tendency, among other statistical or other parameters.

In a further embodiment, one or more of the parameters derivable from said one or more of said candidate heart beats comprise one or more heart rate parameters or heart rate variability parameters, and modifying said neurostimulation comprises identifying a seizure from said one or more heart rate parameters or heart rate variability parameters and administering one or more electrical signals to a neural structure of a patient based on said identification of said seizure. One embodiment of identifying a seizure will be described in more detail with reference to the Third Module, below.

In one embodiment, the beat quality index can be further used to modify an earlier responsive action. For example, after a first value of the beat quality index is used as a basis for performing a responsive action, if a later, second value of the beat quality index indicates a decline in beat quality, the responsive action may be modified in consideration of the possibility that the first value of the beat quality index failed to reflect one or more changes in the quality of the beat data that may have begun at the time the first value was calculated.

For example, if the second value of the beat quality index indicates a decline in beat quality and the responsive action was indicating the occurrence of an epileptic seizure event, the indication may be retrospectively changed to an indication of no occurrence, flagged as based on potentially poor beat data, or the like.

For another example, if the responsive action was delivering a neurostimulation therapy to the patient to treat a medical condition, the neurostimulation therapy may be discontinued, a decision criterion for a future delivery of the neurostimulation therapy may be tightened, or the like.

For yet another example, if the responsive action was warning at least one of a caregiver, the patient, or a physician, a communication of a possibly erroneous warning may be made, or the like.

For yet another example, if the responsive action was logging the beat quality index to a memory, the logged beat quality index value may be changed, flagged as based on potentially poor beat data, or the like.

The time between taking the responsive action and modifying it based on the second value of the beat quality index can vary based on the responsive action, the difference in the first value and the second value of the beat quality index, and/or other parameters that will occur to the person of ordinary skill in the art having the benefit of the present disclosure. For example, if the responsive action was delivering a neurostimulation therapy to the patient to treat a medical condition, wherein the neurostimulation therapy comprises a series of on-times and off-times over a therapy delivery period of 5 minutes, a second value of the beat quality index determined at 6 minutes after the neurostimulation therapy delivery begins can be ignored, and only second values determined at less than 5 minutes after the neurostimulation therapy delivery begins may be considered.

Third Module

In one embodiment, the third module may be operatively coupled to the second module and/or to the first module. The third module may utilize quantified and/or validated beat information from the first and/or second modules to detect a seizure event. In one embodiment, the epileptic seizure events are detected using valid beats, and in one embodiment valid beats accepted as suitable for seizure detection. The detection involves forming a second and a third window and determining a relative heart rate (RHR) based upon a ratio of statistical measures determined for each of the windows. The RHR is then compared to a threshold value for the RHR, and whether the RHR exceeds the RHR threshold is determined. An indication of the occurrence of a seizure event is provided based upon the comparison.

A second window (which may be a time window or a number-of-beats window) is formed for each of the valid beats suitable for seizure detection. In one embodiment, the second window is a backward-looking time window bounded at one end by a first valid beat suitable for seizure detection and including at least one prior valid beat suitable for seizure detection. In one embodiment, the second window may be the same size is the first time window, except that valid beats that have been identified as suitable for seizure detection are used in it instead of simply valid beats. In a particular embodiment, the window is a three second, backward-looking window. A foreground heart rate (FHR) parameter for the second window is determined using a statistical measure of central tendency of heart rate for the beats in the second window.

The second window may comprise a time window or a number-of-beats window. The window may be a simple window (with equal weighting for each time unit or beat unit in the window) or an exponentially forgetting window (with an unequal weighting for each time unit or beat unit in the window, with the most recent time unit or beat unit having the highest weighting and previous time units or beat units having lower weightings taking the form of an exponential decay function). In one embodiment, the second window is a backward-looking, relatively short time window bounded at the present end by a first valid beat, and including at least one prior valid beat. In a particular embodiment, the second window is a three second window bounded by the first valid beat on the present side. In another embodiment, the second window is a three-beat window bounded by the first valid beat on the present side. In another embodiment, the second window is an exponentially forgetting time window weighted to have a decay rate so that the window emphasizes information from a particular time duration (the timescale) or a particular number of beats.

A foreground heart rate parameter for the second window is determined using a statistical measure of central tendency of heart rate or interbeat intervals (which are inversely related to heart rate by the formula: interbeat interval (in seconds)=heart rate (in BPM)/60 for the beats in the second window. While a number of measures (e.g., mean, median) may be used and remain within the scope of the invention, in one embodiment, a target percentile value in a uniform distribution Percentile Tracking Filter applied to the valid beats in the second window is used as the measure of central tendency. In a particular embodiment, the thirtieth ($30^{th}$) percentile of a uniform distribution Percentile Tracking Filter is used as the measure of central tendency. By using a percentile smaller than the $50^{th}$ percentile, the second window will more quickly track decreases in beat interval values, which corresponds to increases in heart rate. Thus, in certain embodiments, this choice of a Percentile Tracking Filter may more quickly identify HR increases than other higher percentile choices (such as the median, the 50th percentile) and more quickly and robustly than other measures of central tendency, such as the mean, regardless whether the mean is computed with or without time-weighting of information.

In one particular embodiment, the Percentile Tracking Filter is an exponentially forgetting Percentile Tracking Filter. Use of exponential forgetting or other time-weighting methods in the measure of central tendency may also provide faster identification of HR changes. Other types of forgetting, non-forgetting, weighted, and unweighted Percentile Tracking Filters (or other measures of central tendency) may also be used. Examples of such filters include, by way of nonlimiting example, order statistic filters and weighted moving average filters. In one embodiment, upper and lower limits or bounds for the uniform distribution used in the foreground Percentile Tracking Filter may be provided. In some embodiments these limits may be adaptively determined based upon the maximum and minimum value of the beat intervals in the second window (i.e., an "adaptive uniform distribution-based Percentile Tracking Filter"), or in another window that may be larger or smaller than the second window.

In another embodiment, the statistical measure of central tendency used for determining the foreground heart rate parameter is a Trimean. The Trimean was developed by Tukey and is defined by the formula $TM=\frac{1}{4}(Q1+2M+Q3)$ where M is the median and Q1 and Q3 are the first and third quartiles. More generally, trimean values using different percentiles than the first and third quartiles may be used through the formula $TM=\frac{1}{4}(H1+2M+H2)$, where M is again the median and H1 and H2 are lower and upper values known as the hinges. In one example, the lower hinge H1 may comprise the $20^{th}$ percentile and the upper hinge H2 may comprise the $80^{th}$ percentile.

The third window is next formed for each of the valid beats suitable for seizure detection. The third window is formed using the first valid beat suitable for seizure detection from the second window, and at least two prior valid beats. The third window may, like the second window, comprise a time or number-of-beats window. In one embodiment, the third window is a backward-looking time window that is longer than the second window, bounded at the present end by the first valid beat from the second window, and includes at least two prior valid beats. In a particular embodiment, the third window is a 500 second window bounded on the present side by the first valid beat from the second window, which in a specific embodiment may be implemented as an exponentially-weighted window with a 500 second timescale, such as may be used in applying a PTF to the time series. In another embodiment, the third window is a 500 beat window bounded on the present side by the first valid beat from the second window. In general, the third window has a larger number of beats than the second window.

A background heart rate (BHR) parameter is determined using a statistical measure of central tendency of heart rate for the beats in the third window. As with the FHR parameter previously discussed, a number of measures of central tendency (e.g., mean, median) may be used and remain within the scope of the invention. In one embodiment, in one embodiment, a target percentile value in a uniform distribution Percentile Tracking Filter applied to the valid beats in the second window is used as the measure of central tendency. In a particular embodiment, the fiftieth ($50^{th}$) percentile of an adaptive, uniform distribution-based Percentile Tracking Filter is used as the measure of central tendency. In one particular embodiment, the Percentile Tracking Filter is an exponentially forgetting Percentile Tracking Filter. Other types of forgetting, non-forgetting, weighted and unweighted Percentile Tracking Filters or other measures of central tendency may be used. Examples of such filters include, by way of nonlimiting example, order statistic filters and weighted moving average filters. Upper and lower limits or bounds for the uniform distribution used in the background Percentile Tracking Filter may be provided. In some embodiments these limits may be adaptively determined based upon the maximum and minimum value of the beat intervals in the second window, or in another window that may be larger or smaller than the second window.

A relative heart rate (RHR) is determined by the ratio of either the FHR and BHR parameters, or the BHR and FHR parameters. The RHR is then compared to a seizure threshold value associated with an epileptic seizure event and it is determined whether the RHR exceeds the seizure threshold. The method further involves indicating the occurrence of a seizure event based upon whether the RHR exceeds the threshold. In some embodiments, a duration constraint may also be imposed and the seizure event is indicated only if the RHR exceeds the threshold for a prescribed period of time (the duration constraint).

In an exemplary embodiment of the present invention, the method further comprises taking a responsive action based upon the identifying the seizure event. The responsive action may include providing a warning and/or notifying the patient or a caregiver, logging the time of a seizure, computing and storing one or more seizure severity indices, or treating the seizure event.

In one embodiment of the present invention, treating the seizure event comprises providing a neurostimulation therapy. The neurostimulation therapy may involve applying an electrical, mechanical, magnetic, electro-magnetic, photonic, acoustic, and/or chemical signal to a neural structure of the body. The neural structure may be a brain, a spinal cord, a peripheral nerve, a cranial nerve, or another neural structure. In a particular embodiment, the responsive action comprises treating the seizure by providing a cranial nerve stimulation therapy. Cranial nerve stimulation has been proposed to treat a number of medical conditions pertaining to or mediated by one or more structures of the nervous system, including epilepsy, movement disorders, depression, anxiety disorders and other neuropsychiatric disorders, dementia, traumatic brain injury, coma, migraine headache, obesity, eating disorders, sleep disorders, cardiac disorders (such as congestive heart failure and atrial fibrillation), hypertension, endocrine disorders (such as diabetes and hypoglycemia), and pain (including neuropathic pain and fibromyalgia), among others. See, e.g., U.S. Pat. Nos. 4,867, 164; 5,299,569; 5,269,303; 5,571,150; 5,215,086; 5,188, 104; 5,263,480; 6,587,719; 6,609,025; 5,335,657; 6,622, 041; 5,916,239; 5,707,400; 5,231,988; and 5,330,515. Despite the numerous disorders for which cranial nerve stimulation has been proposed or suggested as a treatment option, the fact that detailed neural pathways and/or mechanisms of action of stimulation for many (if not all) cranial nerves, and/or the response of such nerves to exogenous stimulation, remain relatively poorly understood, which makes predictions of efficacy and identification of candidates for a therapy for any given disorder difficult or impossible.

In some embodiments, electrical neurostimulation may be provided by implanting an electrical device underneath the skin of a patient and delivering an electrical signal to a nerve such as a cranial nerve. In another alternative embodiment, the signal may be generated by an external pulse generator outside the patient's body, coupled by an RF or wireless link to an implanted electrode.

The cardiac data comprising a fiducial time marker for each of a plurality of heart beats can be gathered by any of a number of techniques. For example, the cardiac data may be gathered by an electrocardiogram (ECG) device. For another example, the cardiac data may be gathered by a cranial nerve stimulator device. In one embodiment, the cardiac data may be related to the R-waves of the beat sequence, such as a time series of R-waves or a series of R-R intervals. Those skilled in the art having benefit of the present disclosure would appreciate that other time series of cardiac waves and/or their fiducial points (e.g., P waves, T waves, etc.) may be used and still remain within the spirit and scope of the present invention.

Data relating to R-waves may be gathered by an ECG device or, in one embodiment, by a vagus nerve stimulator, such as described in U.S. Pat. No. 5,928,272, which is hereby incorporated by reference herein.

Receiving the cardiac data may comprise sensing a time of beat sequence of a patient's heart and generating a time series data stream from said time of the beat sequence. In a further embodiment, receiving the cardiac data of the patient's heart may comprise sensing and time-stamping a plurality of R waves, and generating the time series data stream may comprise determining a series of R-R intervals from the time stamps of the sensed R waves.

In one embodiment, the fiducial time marker is an R wave peak or threshold crossing. The amplitude or height of one or more representative R waves may be used to set a threshold that, when reached or crossed, is registered as a fiducial time marker of a heart beat.

An interbeat interval can be calculated from a pair of said fiducial time markers by any appropriate technique. In one embodiment, the interbeat interval can be calculated by subtracting the time stamp of a first fiducial time marker from the time stamp of a second fiducial time marker following the first. In most existing HR sensing devices (for example, exercise HR monitors), the sensor element involves sensing R-wave peaks, and interbeat intervals comprise R-R intervals constructed from the time stamps for the R-wave peaks. In the present invention, R-R intervals may be used, although any consistently used fiducial marker may be employed, such as P-P intervals, T-T intervals, etc.

Under certain recording conditions, cardiac data may be relatively noisy, and thus, spurious fiducial time markers may be collected and, as a result, spurious interbeat intervals may be generated. Including spurious heart beats and/or interbeat intervals in later steps of the method may lead to erroneous calculations of heart rate, which may in turn result in misidentifications of seizures (false positive detections) and/or failures to identify seizures (false negative detections). As a result, it is desirable to perform one or more data quality checks or routines to eliminate spurious heart beats or interbeat intervals from consideration by later steps of the method. Even where beats are not spurious, not all valid beats may yield acceptable results in cardiac-based seizure detection methods. Accordingly, in some embodiments, valid beats may be subjected to further testing (e.g., dispersion testing in a test window) to determine whether they are suitable for use in detecting seizures.

In one embodiment, a candidate heart beat is subjected to one or more quality tests to determine whether or not it is a valid beat suitable for further analysis, or is an invalid beat and should be ignored. While any number of beat quality tests may be employed, the effects of additional processing time and energy usage upon the power supply in implantable devices may result in a more limited number of tests. In one embodiment, a first beat quality test may be performed by determining if the candidate heart beat reflects an interbeat interval (that is, the interbeat interval calculated as the difference between the time stamp for the candidate heart beat and an immediately preceding heart beat) is not physiologically plausible. A second beat quality test may comprise determining if the candidate heart beat reflects an interbeat interval is so long as to appear to be due to a sinus arrest. A third beat quality test may involve determining if the candidate heart beat reflects an interbeat interval is so short as to appear to be due to noise. A fourth beat quality test may involve calculating the absolute value of the slope of the interbeat interval for the candidate beat and the interbeat interval for the immediately preceding valid beat (defined as the difference between the candidate beat interbeat interval and the interbeat interval defined by the immediately preceding valid beat and the $2^{nd}$ immediately preceding valid beat, divided by the time difference between the candidate beat and the immediately preceding valid beat), and determining whether that slope is too large to be physiologically plausible. In one embodiment, the slope is declared implausible (and the candidate beat declared invalid) if the absolute value of the slope is less than or equal to 0.3. Other thresholds, such as an adaptable threshold, may be used instead of the fixed threshold of 0.3. It will be appreciated that additional or other beat quality tests may be applied, and that only some of the foregoing quality tests may be used. Additionally, it should be noted that HR and R-R intervals can be used interchangeably, since they are related by the simple formula RRi=60/HR, where the R-R interval (RRi) is in seconds and HR is in BPM.

In one embodiment of the invention, the candidate heart beat is declared invalid if the interbeat interval between the candidate beat and the immediately preceding beat is so short that the instantaneous heart rate (IHR), defined as 60/interbeat interval, is greater than about 180 beats per minute (BPM), 200 BPM, or 220 BPM, on the grounds that the human heart cannot have so high an IHR even in intense exertion. In one embodiment, the maximum possible heart rate is calculated as (220–patient's age in years) BPM, from which an interbeat interval corresponding thereto can be calculated and used as the minimum interbeat interval for future calculations for that patient. In one embodiment, the maximum heart rate is defined as 180 BPM. In other embodiments, the patient's actual maximum HR ($HR_{max}$) is determined empirically by testing and the minimum interbeat interval can be either stored directly from the fiducial time marker stream or determined by the formula $RR_{min}$=60/($HR_{max}$).

Conversely, if the interbeat interval associated with a candidate heart beat is so long that the IHR is less than an appropriate lower limit, then the candidate heart beat can be declared invalid, on the grounds the human heart cannot have so low an IHR, even for the heart of a person with extreme cardiovascular fitness at rest. Although 35 BPM is an appropriate lower limit on IHR for the vast majority of epilepsy patients, another lower limit can be established by the physician in consultation with the patient, or determined empirically from recording the patient's actual heart rate from which an interbeat interval can be calculated and used as the maximum interbeat interval for future calculations for that patient.

Where maximum and/or minimum HR or RRi values are determined empirically for an individual patient, appropriate values may be determined, for example, by using a long-term time window (e.g., 6 months, one month, two weeks, or other time period). The maximum rate may be an appropriate function of the actual measured heart rate in the time window. In one embodiment, this may be a target percentage in a Percentile Tracking Filter applied to the beats in the time window.

In another embodiment, if the interbeat interval is so long as to appear to be due to sinus arrest, a candidate heart beat associated with the interbeat interval can be declared invalid on the grounds the IHR cannot decelerate so rapidly from one beat to the next. Generally, if the interbeat interval is more than about 115% of the immediately preceding interbeat interval, then it may likely be that the interbeat interval is too long to reflect a valid beat and thus it can be concluded the candidate heart beat reflects a missed heart beat.

A measured interbeat interval is especially likely to result from one or more missed heartbeats if its duration is some integer (or near-integer) multiple of 100% times the previous valid interbeat interval (e.g., 200% for one missed beat, 300% for two missed beats, etc.). This type of mathematical analysis may also be incorporated into the beat validity testing to specifically identify likely missed heartbeats (e.g.

any measured RRi that is within 200%+/−10% (or other variation threshold) may be identified and logged as being a likely missed beat).

In another embodiment, if the interbeat interval is so short as to appear to be due to noise, a candidate heart beat associated with the interbeat interval can be declared invalid on the grounds the IHR cannot increase so rapidly from one beat to the next. Generally, if the interbeat interval is less than about 65% of the immediately preceding interbeat interval, then it is almost certainly the case that the interbeat interval is too short to reflect a valid beat and thus is can be concluded the candidate heart beat is due to noise or is otherwise not valid.

In another embodiment, if the candidate heart beat yields an interbeat interval having an absolute value of the slope that is too large to be physiologically valid, it can be declared invalid on the grounds the IHR cannot accelerate or decelerate so rapidly.

In one embodiment, identifying valid beats comprises determining if each of the plurality of candidate beats falls within a plausibly physiological interval.

In one embodiment, the beat validity test comprises comparing the candidate beat interval to at least one of an upper and a lower beat interval seizure duration threshold.

In one embodiment, the upper and lower beat interval seizure duration thresholds are derived from at least one of the patient's own heart beat data, and heart beat data from a sample patient population based upon one or more of brain state, sex, age, weight, level of activity, time of day, type of epilepsy, use of drugs or substances (such as food) that affect cardiac function, ambient temperature, body temperature, respiration, and blood pressure, among others.

In one embodiment, the at least one beat interval test comprises:

a) determining that the candidate beat interval corresponds to a heart rate within a range bound by a minimum heart rate and a maximum heart rate;

b) determining that the candidate beat interval is within an acceptable percentage of at least one of the immediately preceding valid beat interval or a recent baseline heart rate in a predetermined time window;

c) determining that the absolute slope of the current candidate beat interval does not correspond to a rate of acceleration or deceleration of heart rate that is physiologically improbable.

In a further embodiment, in the at least one beat interval test, the minimum heart rate is about 35 beats per minute and the maximum heart rate is about 180 beats per minute; the candidate beat interval is not more than about 115 percent of the greater of the immediately preceding valid beat interval or a recent baseline heart rate in a 30 second time window, and is at least about 65 percent of the immediately preceding valid beat interval; and the absolute slope of the current candidate beat interval is ≤0.3. Other thresholds may be used, and thresholds may be altered over time according to the cardiac function of the patient.

Although any one of the grounds set forth above may be sufficient to declare invalid a spurious candidate interbeat interval, and it is most computationally efficient to declare invalid a spurious candidate interbeat interval on the basis of a single ground, two or more of these grounds may be used to declare invalid a spurious candidate interbeat interval to ensure extremely high levels of data reliability for use in a seizure detection algorithm. Noise and artifacts are often coincident with seizures, so the aspects of this invention that enable robust identification of relevant cardiac rate changes in the presence of noise and/or artifacts provide improved methods for ensuring accurate and rapid identification of seizures.

In one embodiment, an index of beat quality may be established to characterize the reliability or robustness of candidate heart beats. The index of beat quality is intended to quantify how well a candidate heart beat has passed one or more beat tests. The index can be used to determine whether a particular test is useful or not (for example, tests that are always passed or always failed may not provide useful information on the whether candidate heart beats are reliable, and may be discontinued or replaced by other tests). The index can also be used as an indication (either alone or with other cardiac parameters) of a seizure. In some patients, seizures are associated with changes in sympathetic and parasympathetic inputs to the heart, as well as muscle artifacts in the case of tonic, clonic, and/or tonic/clonic seizures. Beat quality is lower because of these influences, and a decrease in beat quality index may, in at least some patients, be used to indicate or confirm the occurrence of a seizure.

The index of beat quality may include one or more parameter(s) that may be used to quantify the quality of a candidate beat and/or or a validated beat. The index of beat quality may be used to track data quality to identify periods of time involving relatively good quality or relatively poor data quality. The beat quality tests described herein may also be used to determine the index of beat quality. In one embodiment, a counter may be formed for each candidate heart beat, and the counter is incremented for each test that the candidate heart beat passes. A time stream of data quality points for each beat, or an average or other statistical measure for a plurality of beats, may be used to indicate periods of time in which data quality is high, low, or otherwise within or outside of acceptable limits. In other embodiments, a warning or notification may be provided to a user interface to indicate periods when data quality may need to be addressed, such as when a sensor element or lead has moved or broken. In some cases, seizure detection, logging, or therapy delivery may be automatically disabled until the data quality returns to a certain level.

In one embodiment, the result(s) of the at least one beat validity test can be used to quantify the quality of a candidate heart beat or a fiducial time marker therefor; setting a beat quality index of said candidate heart beat to a first value; testing said candidate heart beat with at least one beat validity test; setting said beat quality index to at least a second value, wherein said second value is indicative of whether said at least one beat validity test was passed or failed; testing said candidate heart beat with at least a second heart beat validity test; setting said beat quality index to at least a third value, wherein said third value is indicative of whether said at least a second heart beat validity test was passed or failed; and performing a responsive action based upon the value of the beat quality index. The responsive action may be selected from the group consisting of:

indicating the occurrence of an epileptic seizure event;

delivering a neurostimulation therapy to the patient to treat a medical condition;

warning at least one of a caregiver, the patient, or a physician; and logging the beat quality index to a memory.

In a particular embodiment, the beat quality index is initialized to a first value (in one example −1 is used as the initial value) prior to receiving any information about a candidate beat. Upon the detection of a candidate beat, the resulting candidate interbeat interval is analyzed using a sequential set of beat interval tests and the beat quality index is increased by 1 for each test passed. Consequently, if there are a total of 5 tests and each are passed, the beat quality index achieves a maximum score of 4. If the first 3 tests are passed and the fourth is failed, the candidate beat can be rejected and given a beat quality score of 2. Then by analyzing the sequence of beat quality indices, one may obtain a wealth of useful information, such as (i) the average beat quality index over a moving window of time, (ii) how often each applied test is passed and failed (providing information about the importance of such test relative to the others, which may be used to optimize computational efficiency of the algorithm for a particular beat detector and typical levels of noise in the sequence of beat detections), (iii) the identification of (and possible warning/logging/other action taken due to) periods of time when heart beat detection has poor accuracy, such as when a long interval of time occurs without any (or many) detected beats being considered valid (i.e., reaching beat quality index of 4), (iv) intervals of time with very good heart beat detection accuracy may be similarly identified.

In another embodiment, a unique value may be provided based upon the outcome of each of the beat validity tests. For example, the BQI may comprise a matrix of binary values having a number of elements equal to the number of beat validity tests. For each test that is failed a 0 may be entered for the element associated with that test, and a 1 may be entered for each test that is passed. Thus, a unique beat quality matrix may be provided for each candidate heart beat that indicates whether each BVT was passed or not.

In one embodiment, the method further comprises storing a time series of beat quality indices of a plurality of said candidate heart beats. In a further embodiment, the method further comprises determining a window beat quality window index comprising a statistical measure of central tendency for the individual beat quality index values of the candidate beats in at least a second window. The statistical measure of said beat quality indices can be a median, a mean, a trimean, a mode, a simple or exponentially-forgetting Percentile Tracking Filter such as described herein, among others. When the value of the window beat quality index is below a threshold value for window beat quality, the value of the beat quality index may be logged and used to indicate that a period of low data quality has occurred.

In one embodiment, the second window can be chosen as a matter of routine experimentation by the person of ordinary skill in the art having the benefit of the present disclosure. In one embodiment, the second window can be essentially the entire time during which the seizure detection method is being performed. In another embodiment, the second window can be a shorter time window. For example, it may be desirable to have the beat quality parameter for a time period encompassing a seizure event as well as relatively short time periods before and/or after a seizure event determined from one or more cardiac parameters. In one embodiment, the second window begins between 30 minutes before a seizure event and 30 minutes after a seizure event and has a duration from about 5 seconds to about 2 hours. The time periods can be optimize by a number of methods, including manual adjustment by a physician, automatically based upon one or more cardiac parameters used for detecting a seizure, or automatically based upon changes (e.g., a decrease) in the beat quality index itself. The seizure window beat quality index may be determined from a statistical measure of central tendency from the individual beat quality indices for the candidate heart beats in the seizure window. In one embodiment, a method for quantifying the quality of a candidate heart beat comprises receiving a reference time marker for a signal portion representative of a candidate heart beat; determining a first quality threshold for validating said candidate heart beat; testing said candidate heart beat with a first beat validity test using at least said first quality threshold; determining a second quality threshold for validating said candidate heart beat; testing said candidate heart beat with a second beat validity test using at least said second quality threshold in response to a determination that said first beat validity test was satisfied by said candidate heart beat; and associating a beat quality certification to said candidate heart beat in response to a determination that said second beat validity test was satisfied by said candidate heart beat.

The information about quality, reliability, and robustness of the heart beat detection information, which results from quantifying beat quality, can also be used in adapting the cardiac-based seizure detection algorithm to improve its performance (e.g., sensitivity, specificity, speed, and information yield). For example, in periods of time that have relatively high beat detection quality index, the system may have high confidence in information regarding cardiac dynamics that is extracted. This may be used to adjust detection thresholds and better learn both physiologic and abnormal cardiac activity patterns for the subject. Other periods in which the beat detection is operating relatively poorly (as measured by the statistics of beat quality index during a moving window), may be avoided for learning such information about cardiac activity patterns. Detection decisions may also be tempered during these times, for example, by raising the detection thresholds to avoid potential detections that could be due to noise in the beat detection system.

In another embodiment, there may be situations where it is desirable to have data, even if of possible low quality, to perform at least some former calculations. Thus, in one embodiment, a constraint removal timer is used for at least one of the at least one beat validity tests. As described above, the constraint removal timer sets a threshold for the time since the last valid beat that, if exceeded, leads to a finding of validity of the candidate heart beat.

Even though declaring invalid spurious candidate heart beats by performing one or more of the above techniques may provide reliable data in most instances, additional testing of candidate heart beats may provide greater reliability and accuracy in cardiac seizure detection algorithms (CSDAs). Because CSDAs must discriminate between heart rate changes associated with seizures and similar increases associated with non-pathologic events (e.g., exercise, state changes such as standing, sitting, or lying down, etc), the accuracy of the CSDA depends in part upon highly accurate heart beat detection. Accordingly, the present invention may involve testing candidate heart beats beyond the immediate interbeat interval. In one embodiment, the invention involves testing candidate heart beats in a time or number-of-beats window to determine if the candidate heart beat would result in excessive dispersion of heart rate within the window. A candidate heart beat forming part of a first window may be discarded if the numbers of beats in the window, the fit error of the beats in the window, or both fall outside of acceptable limits.

For example, if the first time window is five seconds, and the number of heart beats in that time window is greater than about 15 or less than about 3, the number of purported heart beats indicates that the most recent purported heart beat (which may be, for example, the heart beat forming the present side of the window) should be flagged as unsuitable for seizure detection.

In some embodiments, the determination that a particular valid beat is not suitable for seizure detection is only temporary and is limited to a particular window under analysis. That is, if a valid first beat (the most recent beat in the window) fails to pass a window analysis test (along with one or more prior valid beats), the valid first beat may be discarded only in the sense that a detection decision is suspended for the immediate window. The very next valid beat, however (which is now a "new first beat" in a new window under analysis) may result in a window that passes the window analysis test, and a detection decision (using the "new" first beat and the previously "discarded" valid beat) may be allowed.

For another example, a least squares fit may be performed on a candidate heart beat and one or more prior beats in a window. A measure of short-term heart rate variability (HRVst) may be calculated, for example, as the mean square error of the least-squares fit of the heart beats in the window. If the mean squared error of the least squares fit exceeds a threshold, then the purported interbeat intervals can be concluded to possess a fit error so high that the interbeat intervals contain one or more artifacts, and thus the candidate heart beat (which in some embodiments is the only new data point in the window) should be ignored. The person of ordinary skill in the art can perform and/or program a computer to perform a least squares fit as a routine matter. In one embodiment, the threshold is 0.25.

Other measures of short-term heart rate variability may also be used. For example, the absolute prediction error obtained by comparing the current interbeat interval to its predicted value, obtained using past interbeat intervals, can be used as a measure of short-term heart rate variability. The predicted value used for this process could be a constant predictor, a linear predictor, or a nonlinear predictor. A preferred predictor would take into account the distribution of interbeat intervals that have previously occurred when preceded by a sequence of interbeat intervals similar to those measured immediately preceding the moment at which the prediction is to be made. Measures correlated to the amount of curvature present in the interbeat interval sequence (or its counterpart—heart rate sequence) may also be used and correspond to short time action by the body (e.g., sympathetic and parasympathetic activity) to intervene to change the interbeat interval (either by speeding up or slowing down the heart). It is the short-time quantification of changes in the interbeat interval sequence which the window analysis measures are designed to illuminate.

In one embodiment, the first window comprises one of:

a) a time window of from 1 to 10 seconds, bounded on the most recent end by the first valid beat;

b) a number beats window comprising the first valid beat and a number of immediately preceding beats ranging from 1-10; or c) an exponentially forgetting window heavily weighted to the most recent 1 to 10 seconds, bounded on the most recent end by the first valid beat, or the most recent 2-11 beats.

In a further embodiment, the at least one window test comprises at least one of:

a) determining whether the mean square error of a least squares linear fit of the beats in the first window is ≤a predetermined heart rate variability threshold.

In another further embodiment, the first window comprises a time window and the at least one window test comprises determining that the number of valid beats in the window exceeds a lower number of beats threshold.

The at least one window test described above may be used as part of a method of quantifying beat quality, as described above.

Module 3

Valid data suitable for seizure detection, as found by the above techniques, is available for further calculations to detect a seizure event. These further calculations are described in detail in a patent application to the same inventors, U.S. Ser. No. 12/770,562, filed Apr. 29, 2010, with the title "Algorithm For Detecting a Seizure From Cardiac Data," the disclosure of which is incorporated herein by reference.

Upon detection of seizure event, in some embodiments, a responsive action may be taken selected from warning, logging the time of a seizure, computing and storing one or more seizure severity indices, or treating the seizure. These responsive actions are described in detail in U.S. Ser. No. 12/770,562, referred to above.

Although not limited to the following, an exemplary system capable of implementing embodiments of the present invention is described below. FIG. 1A depicts a stylized implantable medical system (IMD) 100 for implementing one or more embodiments of the present invention. An electrical signal generator 110 is provided, having a main body 112 comprising a case or shell with a header 116 for connecting to an insulated, electrically conductive lead assembly 122. The generator 110 is implanted in the patient's chest in a pocket or cavity formed by the implanting surgeon just below the skin (indicated by a dotted line 145), similar to the implantation procedure for a pacemaker pulse generator.

A nerve electrode assembly 125, preferably comprising a plurality of electrodes having at least an electrode pair, is conductively connected to the distal end of the lead assembly 122, which preferably comprises a plurality of lead wires (one wire for each electrode). Each electrode in the electrode assembly 125 may operate independently or alternatively, may operate in conjunction with the other electrodes. In one embodiment, the electrode assembly 125 comprises at least a cathode and an anode. In another embodiment, the electrode assembly comprises one or more unipolar electrodes.

Lead assembly 122 is attached at its proximal end to connectors on the header 116 of generator 110. The electrode assembly 125 may be surgically coupled to the vagus nerve 127 in the patient's neck or at another location, e.g., near the patient's diaphragm or at the esophagus/stomach junction. Other (or additional) cranial nerves such as the trigeminal and/or glossopharyngeal nerves may also be used to deliver the electrical signal in particular alternative embodiments. In one embodiment, the electrode assembly 125 comprises a bipolar stimulating electrode pair 126, 128 (i.e., a cathode and an anode). Suitable electrode assemblies are available from Cyberonics, Inc., Houston, Tex., USA as the Model 302 electrode assembly. However, persons of skill in the art will appreciate that many electrode designs could be used in the present invention. In one embodiment, the two electrodes are wrapped about the vagus nerve, and the electrode assembly 125 may be secured to the vagus nerve 127 by a spiral anchoring tether 130 such as that disclosed in U.S. Pat. No. 4,979,511 issued Dec. 25, 1990 to Reese S. Terry, Jr. Lead assembly 122 may be secured, while retaining the ability to flex with movement of the chest and neck, by a suture connection to nearby tissue (not shown).

In alternative embodiments, the electrode assembly 125 may comprise temperature sensing elements, blood pressure sensing elements, and/or heart rate sensor elements. Other sensors for other body parameters may also be employed.

Both passive and active stimulation may be combined or delivered by a single IMD according to the present invention. Either or both modes may be appropriate to treat a specific patient under observation.

Figure 1B:
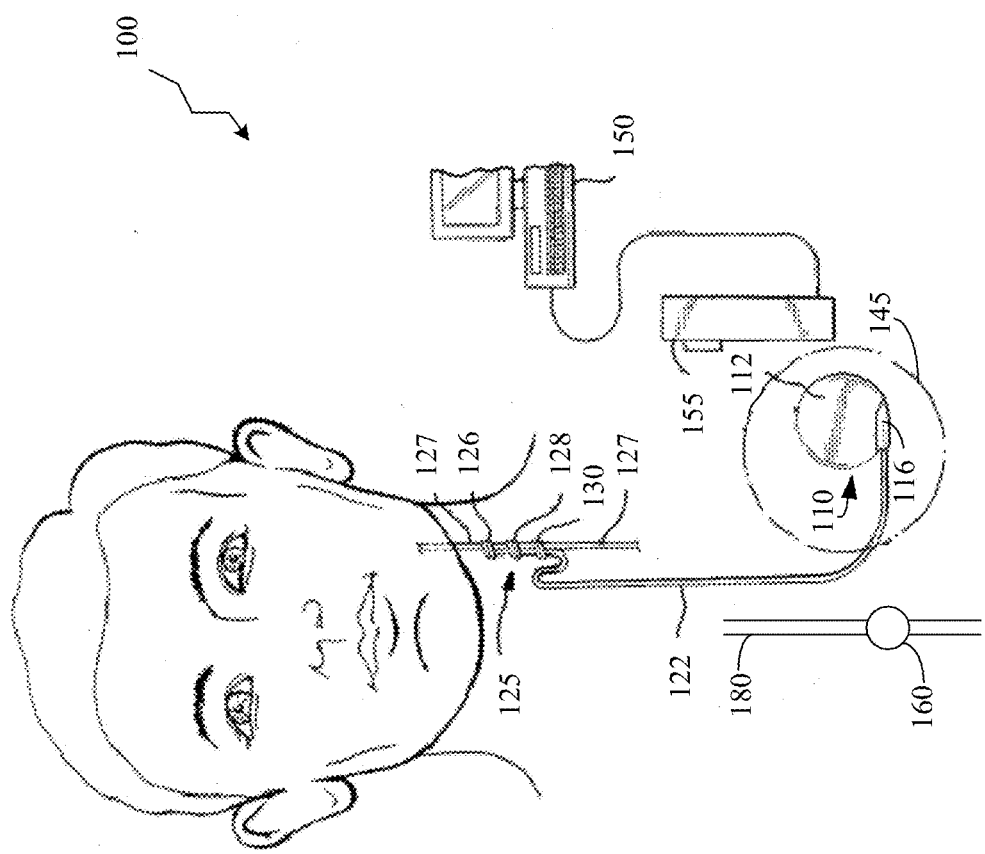
FIG. 1B provides a stylized diagram of a medical device implanted into a patient's body for providing a therapeutic electrical signal to a neural structure of the patient's body, in accordance with one illustrative embodiment of the present invention.
Figure 1C:
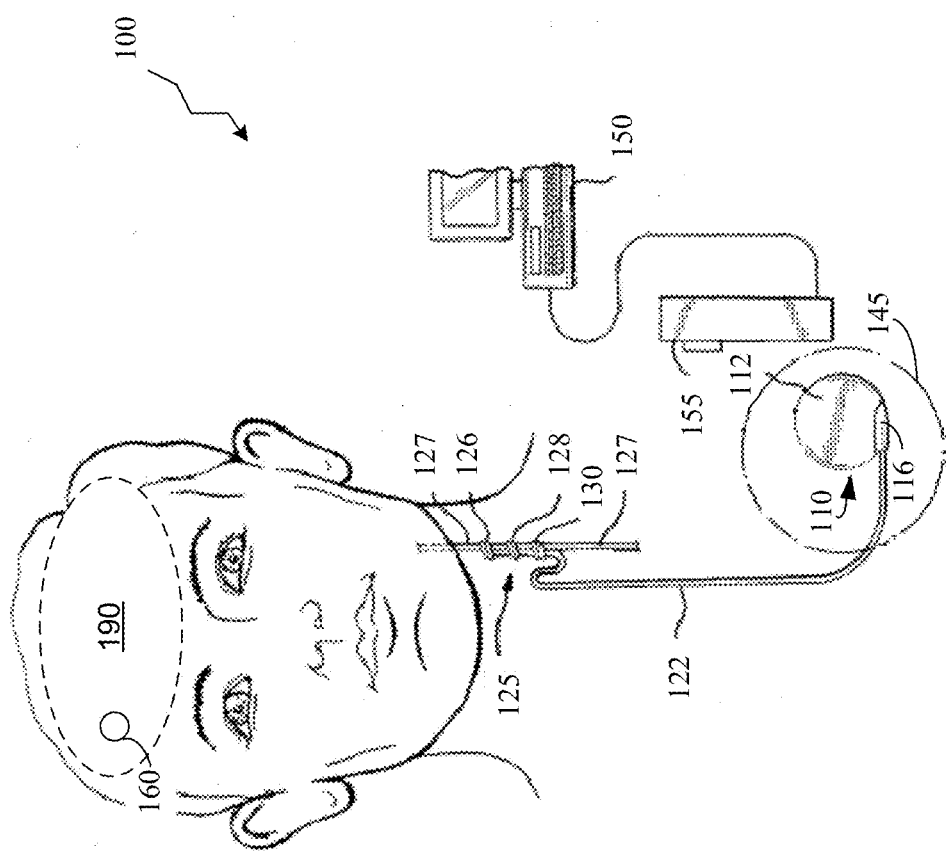
FIG. 1C provides a stylized diagram of a medical device implanted into a patient's body for providing a therapeutic electrical signal to a neural structure of the patient's body, in accordance with one illustrative embodiment of the present invention.

In alternative embodiments, the implantable medical device system further comprises an electrical stimulator comprising an electrode 160 (not to scale) adapted to be coupled to the spinal cord 180 (FIG. 1B) or to a region of the brain 190 (FIG. 1C). The physician can select precise locations for coupling to the spinal cord 180 or brain 190 based on his or her observations of the patient's medical condition, among other values. In various embodiments, the implantable medical device system may comprise one, two, or three of the IMD 100, the spinal cord stimulator, and the brain stimulator.

The electrical pulse generator 110 may be programmed with an external device (ED) such as computer 150 using programming software known in the art. A programming wand 155 may be coupled to the computer 150 as part of the ED to facilitate radio frequency (RF) communication between the computer 150 and the pulse generator 110. The programming wand 155 and computer 150 permit non-invasive communication with the generator 110 after the latter is implanted. In systems where the computer 150 uses one or more channels in the Medical Implant Communications Service (MICS) bandwidths, the programming wand 155 may be omitted to permit more convenient communication directly between the computer 150 and the pulse generator 110.

Turning now to FIGS. 2A-2D, block diagram depictions of exemplary medical devices 200 are provided, in accordance with various illustrative embodiments of the present invention.

In some embodiments, the medical device 200 may be implantable (such as implantable electrical signal generator 110 from FIG. 1), while in other embodiments the medical device 200 may be completely external to the body of the patient.

Figure 2A:
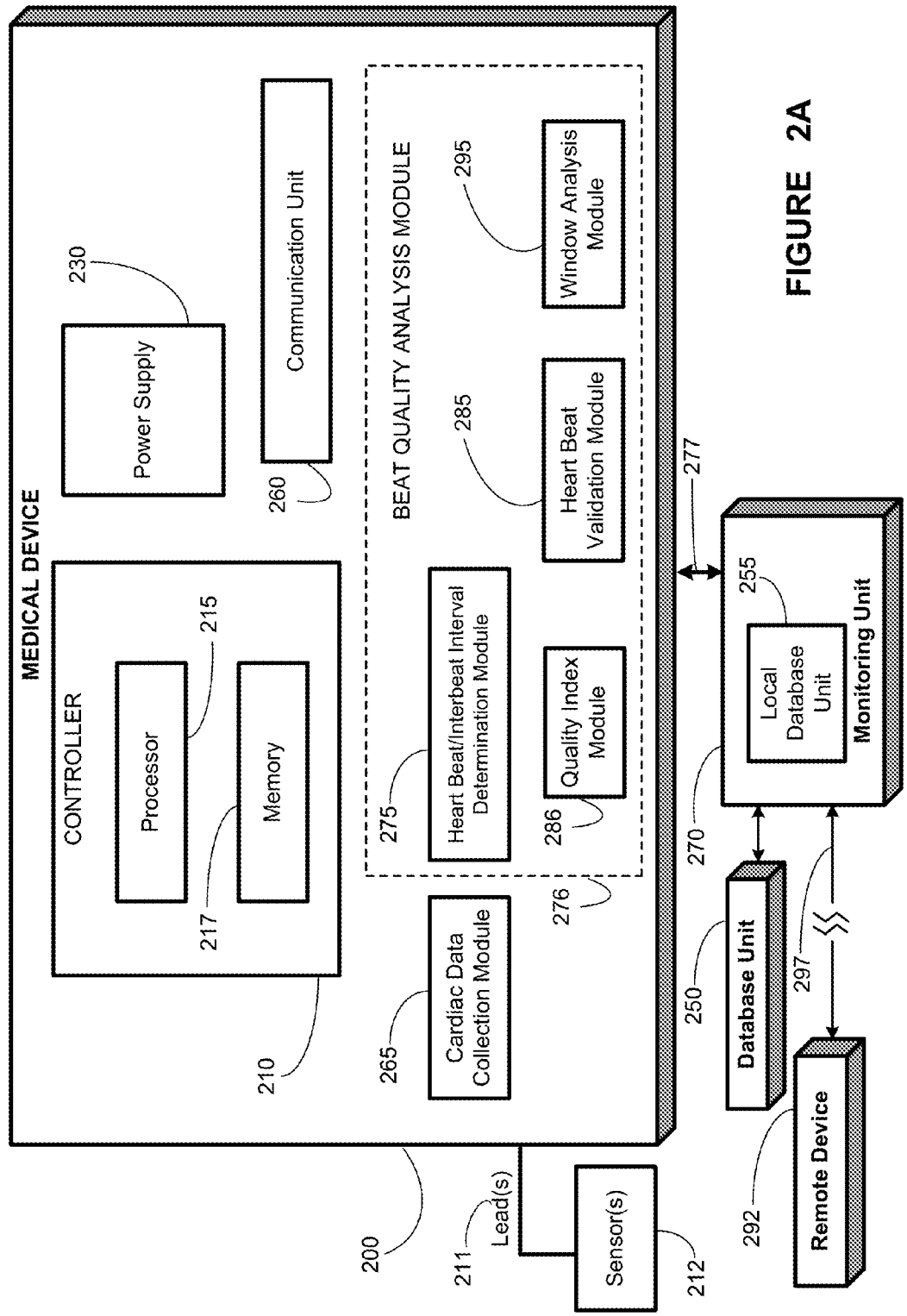
FIG. 2A provides a stylized block diagram of a medical device system that includes a medical device and an external unit, in accordance with one illustrative embodiment of the present invention.

The medical device 200 (such as generator 110 from FIG. 1) may comprise a controller 210 capable of controlling various aspects of the operation of the medical device 200. The controller 210 is capable of receiving internal data or external data, and in one embodiment, is capable of causing a stimulation unit 220 (FIG. 2B) to generate and deliver an electrical signal to target tissues of the patient's body for treating a medical condition. For example, the controller 210 may receive manual instructions from an operator externally, or may cause the electrical signal to be generated and delivered based on internal calculations and programming. In other embodiments, the medical device 200 does not comprise a stimulation unit 220 (FIG. 2A). In either embodiment, the controller 210 is capable of affecting substantially all functions of the medical device 200.

The controller 210 may comprise various components, such as a processor 215, a memory 217, etc. The processor 215 may comprise one or more microcontrollers, microprocessors, etc., capable of performing various executions of software components. The memory 217 may comprise various memory portions where a number of types of data (e.g., internal data, external data instructions, software codes, status data, diagnostic data, etc.) may be stored. The memory 217 may comprise one or more of random access memory (RAM), dynamic random access memory (DRAM), electrically erasable programmable read-only memory (EEPROM), flash memory, etc.

Figure 2B:
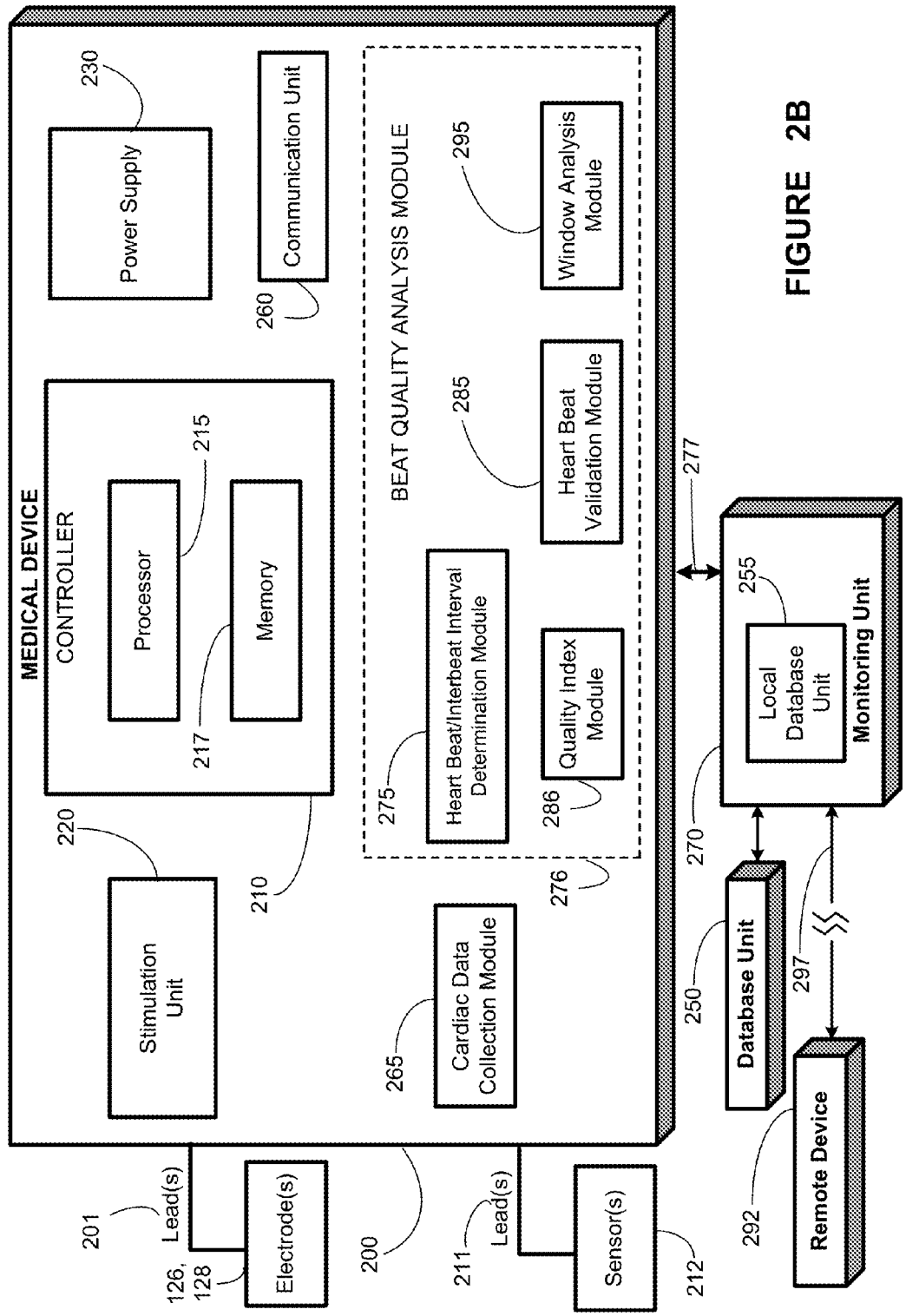
FIG. 2B provides another stylized block diagram of a medical device system that includes a medical device and an external unit, in accordance with one illustrative embodiment of the present invention.

As stated above, in one embodiment, the medical device 200 may also comprise a stimulation unit 220 capable of generating and delivering electrical signals to one or more electrodes 126, 128 via leads 201 (FIG. 2B). A lead assembly such as lead assembly 122 (FIG. 1) may be coupled to the medical device 200. Therapy may be delivered to the leads 201 comprising the lead assembly 122 by the stimulation unit 220 based upon instructions from the controller 210. The stimulation unit 220 may comprise various circuitry, such as electrical signal generators, impedance control circuitry to control the impedance "seen" by the leads, and other circuitry that receives instructions relating to the delivery of the electrical signal to tissue. The stimulation unit 220 is capable of delivering electrical signals over the leads 201 comprising the lead assembly 122. As should be apparent, in certain embodiments, the medical device 200 does not comprise a stimulation unit 220, lead assembly 122, or leads 201.

In other embodiments, a lead 201 is operatively coupled to an electrode, wherein the electrode is adapted to couple to at least one of a portion of a brain structure of the patient, a cranial nerve of a patient, a spinal cord of a patient, a sympathetic nerve structure of the patient, or a peripheral nerve of the patient.

The medical device 200 may also comprise a power supply 230. The power supply 230 may comprise a battery, voltage regulators, capacitors, etc., to provide power for the operation of the medical device 200, including delivering the therapeutic electrical signal. The power supply 230 comprises a power source that in some embodiments may be rechargeable. In other embodiments, a non-rechargeable power source may be used. The power supply 230 provides power for the operation of the medical device 200, including electronic operations and the electrical signal generation and delivery functions. The power supply 230 may comprise a lithium/thionyl chloride cell or a lithium/carbon monofluoride (LiCFx) cell if the medical device 200 is implantable, or may comprise conventional watch or 9V batteries for external (i.e., non-implantable) embodiments. Other battery types known in the art of medical devices may also be used.

The medical device 200 may also comprise a communication unit 260 capable of facilitating communications between the medical device 200 and various devices. In particular, the communication unit 260 is capable of providing transmission and reception of electronic signals to and from a monitoring unit 270, such as a handheld computer or PDA that can communicate with the medical device 200 wirelessly or by cable. The communication unit 260 may include hardware, software, firmware, or any combination thereof.

The medical device 200 may also comprise one or more sensor(s) 212 coupled via sensor lead(s) 211 to the medical device 200. The sensor(s) 212 are capable of receiving signals related to a physiological parameter, such as the patient's heart beat, blood pressure, and/or temperature, and delivering the signals to the medical device 200. In one embodiment, the sensor(s) 212 may be the same as implanted electrode(s) 126, 128 (FIG. 1). In other embodiments, the sensor(s) 212 are external structures that may be placed on the patient's skin, such as over the patient's heart or elsewhere on the patient's torso.

In one embodiment, the medical device 200 may comprise a cardiac data collection module 265 that is capable of collecting cardiac data comprising fiducial time markers of each of a plurality of heart beats. The cardiac data collection module 265 may also process or condition the cardiac data. The cardiac data may be provided by the sensor(s) 212. The cardiac data collection module 265 may be capable of performing any necessary or suitable amplifying, filtering, and performing analog-to-digital (A/D) conversions to prepare the signals for downstream processing. The cardiac data collection module, in one embodiment, may comprise software module(s) that are capable of performing various interface functions, filtering functions, etc., to process fiducial time markers of each of a plurality of heart beats. In another embodiment the cardiac data collection module 265 may comprise hardware circuitry that is capable of performing these functions. In yet another embodiment, the cardiac data collection module 265 may comprise hardware, firmware, software and/or any combination thereof. A more detailed illustration of the cardiac data collection module 265 is provided in FIG. 3A and accompanying description below.

The cardiac data collection module 265 is capable of collecting cardiac data comprising fiducial time markers of each of a plurality of candidate heart beats and providing the collected cardiac data to an heart beat/interval determination module 275. Based upon the signals processed by the cardiac data collection module 265, the heart beat/interval determination module 275 may calculate an interbeat interval from a consecutive pair of said fiducial time markers and store such interbeat interval or forward it on for further processing/analysis. The heart beat/interval determination module 275 may comprise software module(s) that are capable of performing various interface functions, filtering functions, etc., to calculate interbeat intervals. In another embodiment the heart beat/interval determination module 275 may comprise hardware circuitry that is capable of performing these functions. In yet another embodiment, the heart beat/interval determination module 275 may comprise hardware, firmware, software and/or any combination thereof. Further description of the heart beat/interval determination module 275 is provided in FIG. 3B and accompanying description below.

The heart beat/interval determination module 275 is capable of calculating an interbeat interval from a consecutive pair of said fiducial time markers and providing the interbeat interval to the heart beat validation module 285. Based upon the interbeat interval received by the heart beat validation module 285, it performs any operations desired to identify invalid interbeat intervals and discard them. For example, the heart beat validation module 285 may discard the candidate heart beat if the interbeat interval formed from the candidate heart beat and the immediately preceding valid beat is not physiologically valid, is so long as to appear to be due to a missed heart beat, is so short as to appear to be due to noise, has an absolute value of the slope of the interbeat interval that is too large to be physiologically valid, or two or more thereof. The heart beat validation module 285 may comprise software module(s) that are capable of performing various interface functions, filtering functions, etc., to discard invalid beats. In another embodiment the heart beat validation module 285 may comprise hardware circuitry that is capable of performing these functions. In yet another embodiment, the heart beat validation module 285 may comprise hardware, firmware, software and/or any combination thereof. Further description of the heart beat validation module 285 is provided in FIG. 3C and accompanying description below.

The heart beat validation module 285 is capable of declaring invalid beats and forwarding a plurality of heart beats accepted as valid to window analysis module 295. Based upon the plurality of valid beats received by the window analysis module 295, it performs any operations desired to perform further testing of the valid beats in one or more heart beat windows to identify valid beats suitable for seizure detection. For example, the window analysis module 295 may discard a plurality of valid beats as unsuitable for seizure detection if the number, the heart rate variability, or both of a window analysis performed on the valid beat in a backward-looking window fail to pass a number-of-beats threshold and/or a HRV threshold. The window analysis module 295 may comprise software module(s) that are capable of performing various interface functions, filtering functions, etc., to reject valid beats as unsuitable for seizure detection. In another embodiment the window analysis module 295 may comprise hardware circuitry that is capable of performing these functions. In yet another embodiment, the window analysis module 295 may comprise hardware, firmware, software and/or any combination thereof. Further description of the window analysis module 295 is provided in FIG. 3D and accompanying description below.

The window analysis module 295 is capable of ignoring one or more valid beats that are unsuitable for seizure detection, and forwarding a plurality of valid interbeat intervals that are suitable for seizure detection to foreground/background module 297 (FIG. 3E). (The terms "flagging," "ignoring," and "discarding" may be used herein to refer to not using one or more valid beats for seizure detection). The foreground/background module 297 is capable of calculating various heart rates, slopes of heart rate series, durations of heart rates or slopes of heart rates above various seizure threshold values, or the like and forwarding the calculated information to seizure detection module 299 (FIG. 3F). Based upon the calculated information received by the seizure detection module 299, it performs any operations desired to identify a seizure event. More detail regarding the foreground/background module 297 and the seizure identification module 299 is provided in U.S. Ser. No. 12/770,562, referred to above.

FIGS. 2A-2B depict the heart beat/interval determination module 275, the heart beat validation module 285, the window analysis module 295, along with a beat quality index module 286, as components of a beat quality analysis module 276. The beat quality index module 286 is capable of setting an initial value of a beat quality index for a candidate heart beat, receiving information from heart beat validation module 285 about beat validity test(s) passed and/or failed by a candidate heart beat, receiving information from window analysis module 295 about window test(s) passed and/or failed by a window comprising a valid beat, and adjusting the value of the beat quality index based on the received information. As should be apparent, even though various modules are shown as components of beat quality analysis module 276, they may also be capable of functions not related to quantifying beat quality.

Figure 2C:
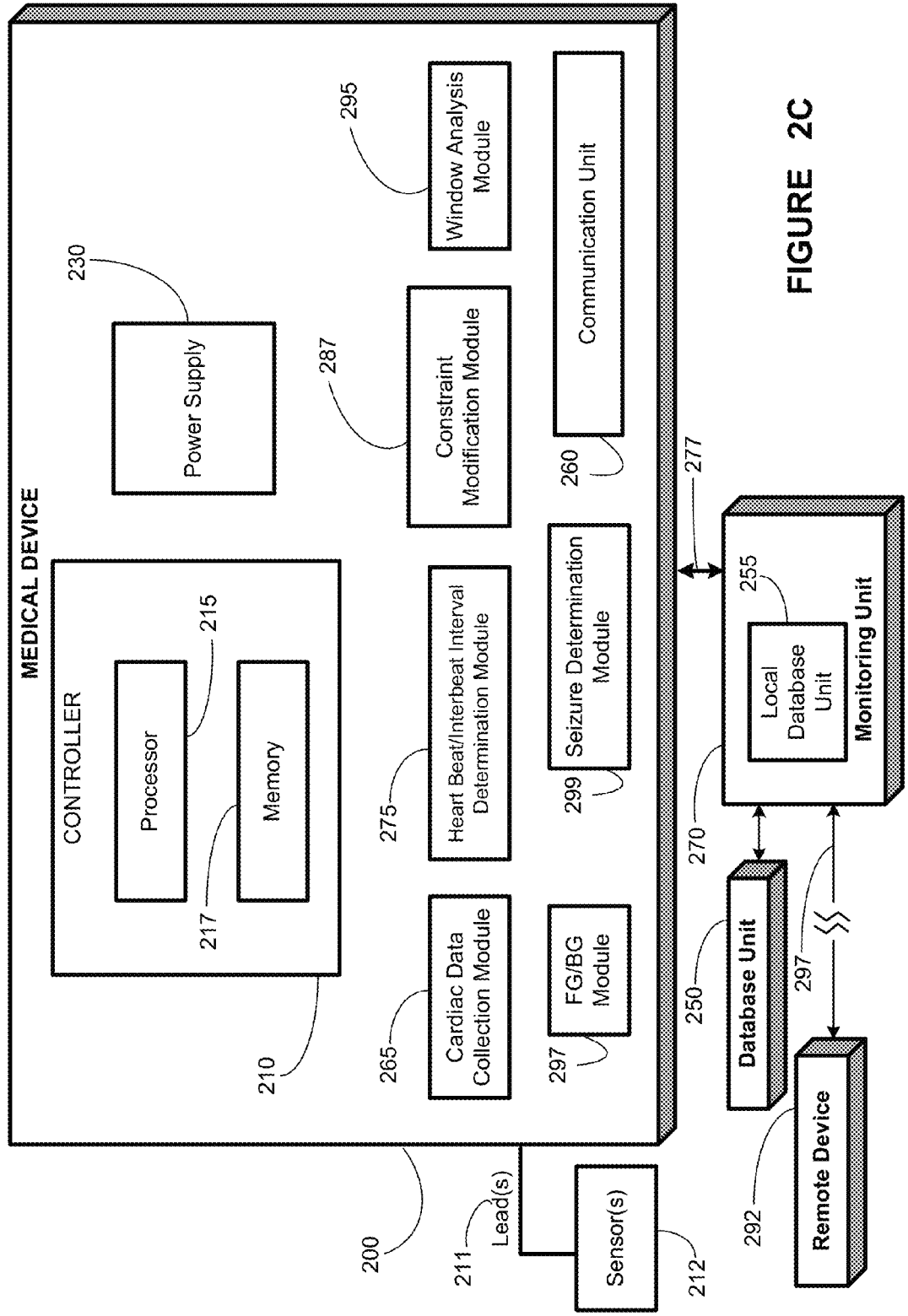
FIG. 2C is a block diagram of a medical device system that includes a medical device and an external unit, in accordance with one illustrative embodiment of the present invention.
Figure 2D:
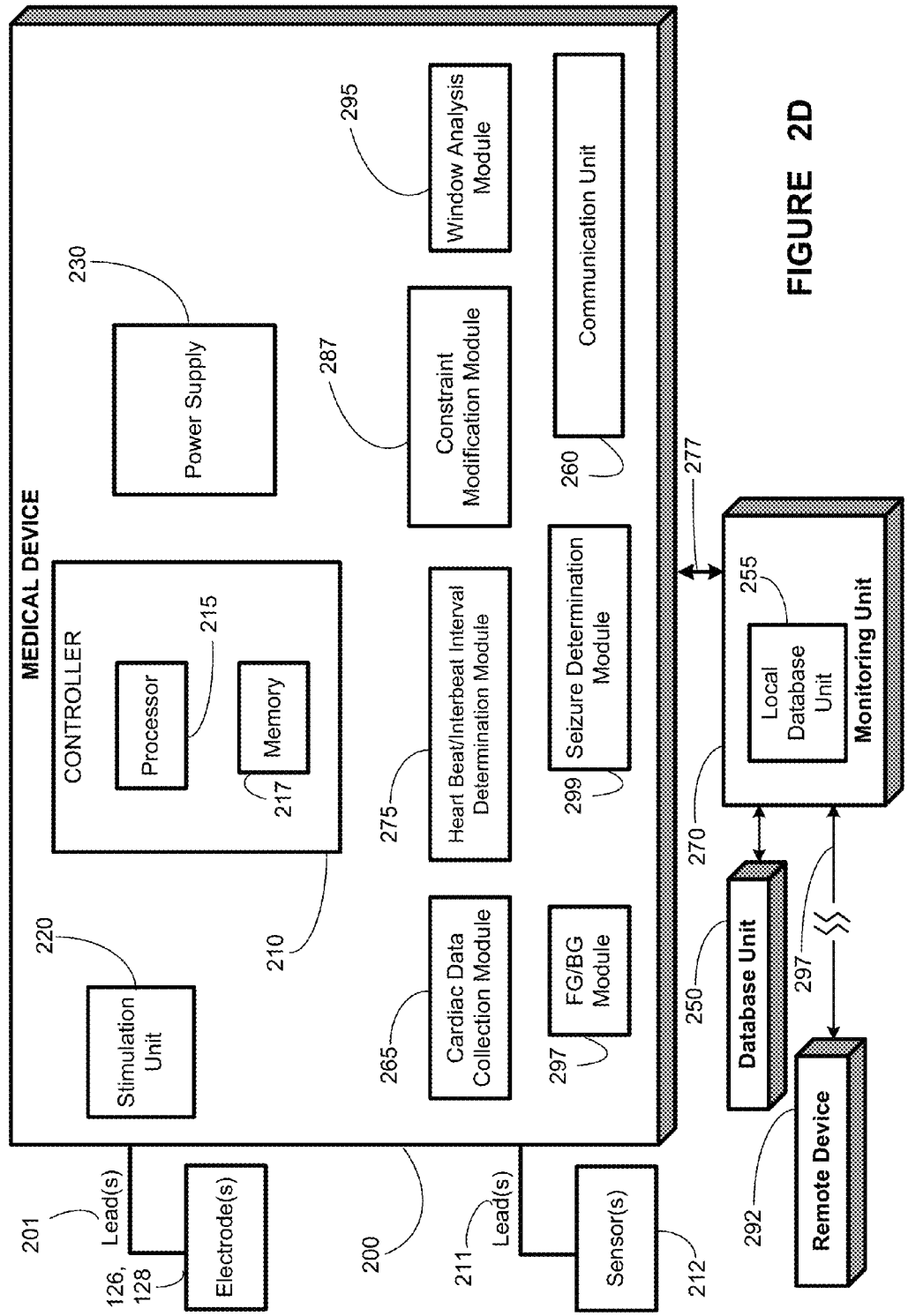
FIG. 2D is a block diagram of a medical device system that includes a medical device and an external unit, in accordance with one illustrative embodiment of the present invention.

In another embodiment, in addition to the heart beat/interval determination module 275, the heart beat validation module 285, and the window analysis module 295, FIGS. 2C-2D depict a constraint modification unit 287. The constraint modification unit 287 modifies at least one constraint for one or more of the at least one beat validity tests performed by the heart beat/interbeat interval determination module 275 and determines, in the event of a finding of an invalid beat by the beat validity test(s) (i.e., failure of a candidate heart beat to pass one or more tests), if the time since the last valid beat is greater than the threshold. If the time since the last valid beat is greater than the threshold, the constraint modification unit 287 modifies the constraint, such as by relaxing the constraint or tightening the constraint. This may make the test easier or more difficult, respectively, for future candidate beats to pass. If the candidate heart beat was found valid by the test(s), the constraint modification unit 287 resets the timer since the last valid beat (because the candidate heart beat has become the last valid beat) and, if the constraint is modified during timing by the timer, resets the constraint to its initial value.

In addition to components of the medical device 200 described above, an implantable medical system may comprise a storage unit to store an indication of at least one of seizure or an increased risk of a seizure or an index of beat quality. The storage unit may be the memory 217 of the medical device 200, another storage unit of the medical device 200, or an external database, such as the local database unit 255 or a remote database unit 250. The medical device 200 may communicate the indication via the communications unit 260. Alternatively or in addition to an external database, the medical device 200 may be adapted to communicate the indication to at least one of a patient, a caregiver, or a healthcare provider.

In various embodiments, one or more of the units or modules described above may be located in a monitoring unit 270 or a remote device 292, with communications between that unit or module and a unit or module located in the medical device 200 taking place via communication unit 260. For example, in one embodiment, one or more of the cardiac data collection module 265, the heart beat/interval determination module 275, the heart beat validation module 285, the window analysis module 295, the foreground/background module 297, the beat quality index module 286, the beat quality analysis module 276, the constraint modification unit 287, or the seizure detection module 299 may be external to the medical device 200, e.g., in a monitoring unit 270. Locating one or more of the cardiac data collection module 265, the heart beat/interval determination module 275, the heart beat validation module 285, the window analysis module 295, the foreground/background module 297, the beat quality index module 286, the beat quality analysis module 276, the constraint modification unit 287, or the seizure detection module 299 outside the medical device 200 may be advantageous if the calculation(s) is/are computationally intensive, in order to reduce energy expenditure and heat generation in the medical device 200 or to expedite calculation.

The monitoring unit 270 may be a device that is capable of transmitting and receiving data to and from the medical device 200. In one embodiment, the monitoring unit 270 is a computer system capable of executing a data-acquisition program. The monitoring unit 270 may be controlled by a healthcare provider, such as a physician, at a base station in, for example, a doctor's office. In alternative embodiments, the monitoring unit 270 may be controlled by a patient in a system providing less interactive communication with the medical device 200 than another monitoring unit 270 controlled by a healthcare provider. Whether controlled by the patient or by a healthcare provider, the monitoring unit 270 may be a computer, preferably a handheld computer or PDA, but may alternatively comprise any other device that is capable of electronic communications and programming, e.g., hand-held computer system, a PC computer system, a laptop computer system, a server, a personal digital assistant (PDA), an Apple-based computer system, a cellular telephone, etc. The monitoring unit 270 may download various parameters and program software into the medical device 200 for programming the operation of the medical device, and may also receive and upload various status conditions and other data from the medical device 200. Communications between the monitoring unit 270 and the communication unit 260 in the medical device 200 may occur via a wireless or other type of communication, represented generally by line 277 in FIG. 2. This may occur using, e.g., wand 155 (FIG. 1) to communicate by RF energy with an implantable signal generator 110. Alternatively, the wand may be omitted in some systems, e.g., systems in which the MD 200 is non-implantable, or implantable systems in which monitoring unit 270 and MD 200 operate in the MICS bandwidths.

In one embodiment, the monitoring unit 270 may comprise a local database unit 255. Optionally or alternatively, the monitoring unit 270 may also be coupled to a database unit 250, which may be separate from monitoring unit 270 (e.g., a centralized database wirelessly linked to a handheld monitoring unit 270). The database unit 250 and/or the local database unit 255 are capable of storing various patient data. These data may comprise patient parameter data acquired from a patient's body, therapy parameter data, seizure severity data, and/or therapeutic efficacy data. The database unit 250 and/or the local database unit 255 may comprise data for a plurality of patients, and may be organized and stored in a variety of manners, such as in date format, severity of disease format, etc. The database unit 250 and/or the local database unit 255 may be relational databases in one embodiment. A physician may perform various patient management functions (e.g., programming parameters for a responsive therapy and/or setting thresholds for one or more detection parameters) using the monitoring unit 270, which may include obtaining and/or analyzing data from the medical device 200 and/or data from the database unit 250 and/or the local database unit 255. The database unit 250 and/or the local database unit 255 may store various patient data.

One or more of the blocks illustrated in the block diagram of the medical device 200 in FIG. 2A or FIG. 2B, may comprise hardware units, software units, firmware units, or any combination thereof. Additionally, one or more blocks illustrated in FIG. 2A-B may be combined with other blocks, which may represent circuit hardware units, software algorithms, etc. Additionally, any number of the circuitry or software units associated with the various blocks illustrated in FIG. 2A-B may be combined into a programmable device, such as a field programmable gate array, an ASIC device, etc.

The medical device system of one embodiment of the present invention provides for software module(s) that are capable of acquiring, storing, and processing various forms of data, such as patient data/parameters (e.g., physiological data, side-effects data, heart rate data, breathing rate data, brain-activity parameters, disease progression or regression data, quality of life data, etc.) and therapy parameter data. Therapy parameters may include, but are not limited to, electrical signal parameters (e.g., frequency, pulse width, wave shape, polarity, on-time, off-time, etc.) that define therapeutic electrical signals delivered by the medical device in response to the detection of the seizure, medication type, dose, or other parameters, and/or any other therapeutic treatment parameter.

In one embodiment, the present invention may include coupling of at least one electrode to each of two or more cranial nerves. (In this context, two or more cranial nerves mean two or more nerves having different names or numerical designations, and do not refer to the left and right versions of a particular nerve). In one embodiment, at least one electrode may be coupled to either or both vagus nerves or a branch of either or both vagus nerves. The term "operatively" coupled may include directly or indirectly coupling. Each of the nerves in this embodiment or others involving two or more cranial nerves may be stimulated according to particular activation modalities that may be independent between the two nerves.

Returning to systems for providing cranial nerve stimulation, such as that shown in FIG. 1, and as stated above, alternatively or in addition to a responsive treatment, if any, cranial nerve stimulation may be provided on a continuous basis to alleviate chronic aspects of the patient's medical disorder. Where cranial nerve stimulation is provided based solely on programmed off-times and on-times, the stimulation may be referred to as passive, inactive, open-loop, non-feedback, or non-contingent stimulation. In contrast, stimulation may be triggered by one or more feedback loops according to changes in the body or brain of the patient. This stimulation may be referred to as active, closed-loop, feedback-loop, or contingent stimulation. In one embodiment, feedback-loop stimulation may be manually-triggered stimulation, in which the patient manually causes the activation of a pulse burst outside of the programmed on-time/off-time cycle at a time of the patient's choosing, for example, in response to a sensation of an impending seizure. The patient may manually activate an implantable signal generator 110 to stimulate the cranial nerve, such as vagus nerve 127, to treat an acute episode of a medical condition, e.g., a seizure. The patient may also be permitted to alter the intensity of the signals applied to the cranial nerve within limits established by the physician.

Patient activation of a medical device 100 may involve use of an external control magnet for operating a reed switch in an implanted device, for example. Certain other techniques of manual and automatic activation of implantable medical devices are disclosed in U.S. Pat. No. 5,304,206 to Baker, Jr., et al. ("the '206 patent"). According to the '206 patent, means for manually activating or deactivating the electrical signal generator 110 may include a sensor such as piezoelectric element mounted to the inner surface of the generator case and adapted to detect light taps by the patient on the implant site. One or more taps applied in fast sequence to the skin above the location of the electrical signal generator 110 in the patient's body may be programmed into the implanted medical device 100 as a signal for intensification of the electrical signal. Two taps spaced apart by a slightly longer duration of time may be programmed into the medical device 100 to indicate a desire to de-intensify the electrical signal. The patient may be given limited control over operation of the device to an extent which may be determined by the program or entered by the attending physician. The patient may also activate the medical device 100 using other suitable techniques or apparatus.

In one embodiment, the medical device 200 may also be capable of detecting a manual input from the patient. The manual input may include a magnetic signal input, a tap input, a wireless data input to the medical device 200, etc.

Figure 3A:
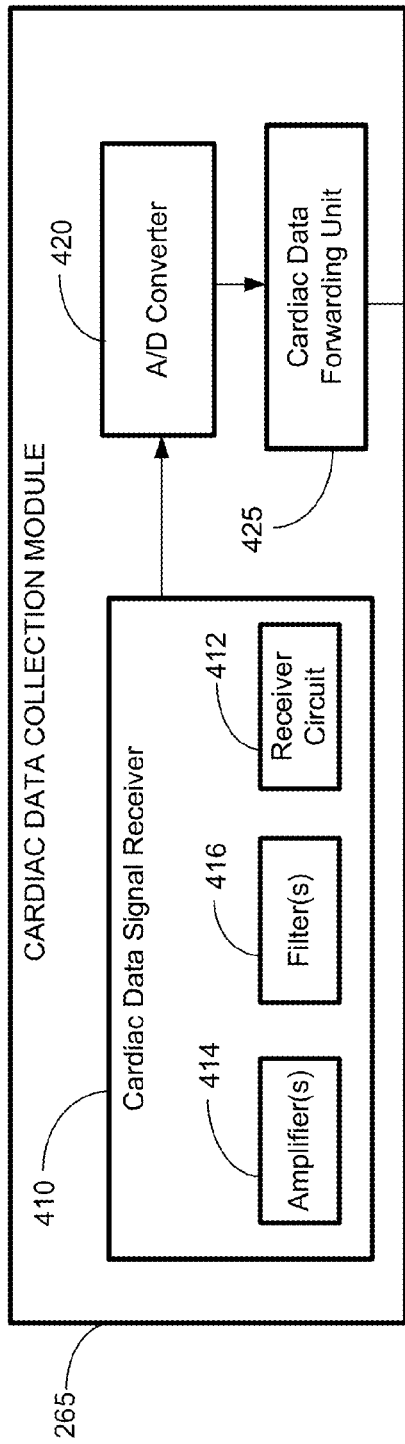
FIG. 3A is a stylized block diagram of a cardiac data collection module of a medical device, in accordance with one illustrative embodiment of the present invention.

Turning now to FIG. 3A, a more detailed stylized depiction of the cardiac data collection module 265 of FIG. 2, in accordance with one illustrative embodiment of the present invention is depicted. In one embodiment, the cardiac data collection module 265 comprises a cardiac data signal receiver 410, an analog-to-digital converter (A/D Converter) 420, and a cardiac data forwarding unit 425. The cardiac data signal receiver 410 is capable of receiving the signals from the sensor(s) 212 via receiver circuit 412. The signal that is received by the receiver circuit 412 is processed and filtered to enable the data to be further analyzed and/or processed for determining a fiducial time marker of a heart beat.

The cardiac data signal receiver 410 may comprise amplifier(s) 414 and filter(s) 416. The amplifiers 414 are capable of buffering and amplifying the input signals received by the receiver circuit 412. In many cases, the heart beat signal may be attenuated and may be characterized by significantly low amplitude responses and signal noise. The amplifier(s) 414 are capable of buffering (amplification by unity) and amplifying the signals for further processing. In one embodiment, the amplifier 414 may comprise op amp circuit(s), digital amplifier(s), buffer amplifiers, and/or the like.

The cardiac data signal receiver 410 may also comprise one or more filters 416. The filters 416 may comprise analog filter(s), digital filter(s), filters implemented by digital signal processing (DSP) means or methods, etc. The amplified and buffered heart beat signal may be filtered to remove various noise signals residing on the heart beat signal. The filter 416, for example, is capable of filtering out various noise signals caused by external magnetic fields, electrical fields, noise resulting from physiological activity, etc. Filtering, signal noise due to breathing or other signals produced by the patient's body may be filtered.

The cardiac data signal receiver 410 provides amplified, filtered signals to the A/D converter 420. The A/D converter 420 performs an analog-to-digital conversion for further processing. The A/D converter 420 may be one type of a plurality of converter types with various accuracies, such as an 8-bit converter, a 12-bit converter, a 24-bit converter, a 32-bit converter, a 64-bit converter, a 128-bit converter, a 256-bit converter, etc. The converted digital signal is then provided to a cardiac data forwarding unit 425. In an alternative embodiment, the A/D conversion may be performed prior to filtering or signal processing of the heart beat signal. The converted digital signal is then provided to a cardiac data forwarding unit 425.

The cardiac data forwarding unit 425 is capable of organizing, correlating, stacking, and otherwise processing the digitized, buffered, and filtered cardiac data and forwarding it to the heart beat/interval determination module 275. The cardiac data forwarding unit 425 may correlate various time stamps with the heart beat signal to provide a time of beat sequence of the patient's heart, or more accurately a time of beat sequence of candidate heart beats subject to further processing and/or testing in, e.g., subsequent modules 275, 285, 297, 295, and 299. The digital signals issuing from the cardiac data forwarding unit 425, comprising a time stamp sequence of candidate heart beats, may then be forwarded to the heart beat/interval calculation module 275.

Figure 3B:
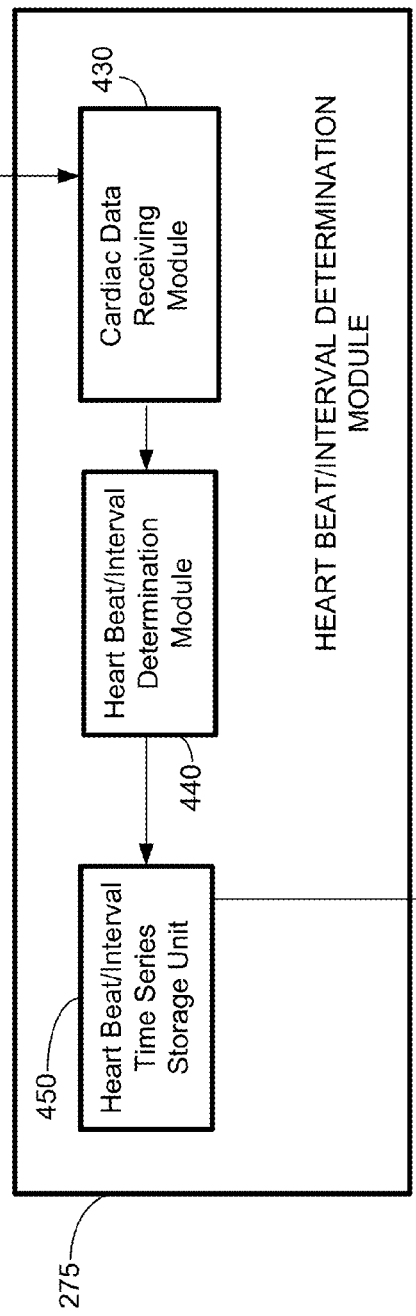
FIG. 3B is a stylized block diagram of an heart beat/interval determination module of a medical device, in accordance with one illustrative embodiment of the present invention.

Turning now to FIG. 3B, a more detailed stylized depiction of the heart beat/interval determination module 275 of FIG. 2, in accordance with one illustrative embodiment of the present invention, is depicted. The heart beat/interval determination module 275 may comprise a cardiac data receiving module 430, for receiving a time stamp sequence of candidate heart beats, a heart beat interval determination module 440, and a heart beat/interval time series storage unit 450. The heart beat/interval determination module 275 may determine interbeat intervals for adjacent candidate heart beats as they appear in the time series of signals via the cardiac data receiving module 430. For example, cardiac data receiving module 430 may characterize certain data points in the time series of signals as being fiducial time markers corresponding to, for example, the start, the peak, or the end of an R-wave of a patient's cardiac cycle.

Once fiducial time markers are determined from the time series of signals, the heart beat interval determination module 440 may determine the interval between consecutive beats ("interbeat interval") and forward this information to heart beat/interval time series storage 450, which may store one or both of a time stamp series associated with fiducial markers indicating of an individual heart beat and a time stamp series of adjacent interbeat intervals. In some embodiments, beat interval determination module 440, may also calculate other values from the time sequence of candidate heart beats, such as an instantaneous HR.

Turning now to FIG. 3C, a more detailed stylized depiction of the heart beat validation module 285 of FIG. 2, in accordance with one illustrative embodiment of the present invention, is depicted. The heart beat validation module 285 may receive various data from the heart beat/interval determination module 275. Heat beat validation module 285 tests candidate heart beats and/or intervals received from heart beat/interval calculation module 275 to one or more beat validity tests. The outcome of the beat validity tests may be used to discard candidate heart beats from further analysis, and the valid beats are then passed to window analysis module 295.

In the depiction shown in FIG. 3C, data received from the heart beat/interval determination module 275 is forwarded to heart beat validation module 285. The data is initially sent to a physiologically plausible heart beat interval unit 505, which determines whether the interbeat interval is physiologically plausible (i.e., whether an interbeat interval determined from a candidate heart beat and an immediately preceding beat is within a range typically seen in human physiology). In one embodiment, this may involve comparing the interbeat interval for the candidate heart beat with an upper and a lower beat interval duration threshold and declaring invalid the candidate heart beat as invalid if it lies outside of the upper and lower thresholds. In one embodiment this corresponds to ensuring that the interbeat interval corresponds to a heart rate of between about 35 BPM and about 180 BPM.

Valid beats may from physiologically plausible heart beat interval unit 505 are then be forwarded to apparent missed heartbeat unit 510, which determines whether the interbeat interval is so long as to appear to be due to a missed heartbeat and therefore invalid. In one embodiment, the apparent missed heartbeat unit 510 tests the interbeat interval for the candidate heart beat to ensure that the interval is not more than about 115 percent (or another acceptable percentage exceeding 100%) of the greater of 1) the immediately preceding valid beat interval or 2) a recent baseline heart rate. Other tests may used, so long as the test ensures that the beat interval is not excessively long and likely due to a missed beat. Candidate beats failing the test(s) of the apparent missed heart beat unit 510 are discarded, and the remaining beats are forwarded to apparent noise unit 515.

In contrast to apparent missed heart beat unit 510—which tests candidate heart beat to ensure that the interbeat interval is not excessively long—apparent noise unit 515 tests candidate heart beats to ensure that the interbeat interval associated with the candidate beat is not so short as to appear to be due to noise, in which case the candidate heart beat is discarded. In one embodiment, the apparent noise unit 515 tests the interbeat interval for the candidate heart beat to ensure that the interval is at least a certain minimum length. In particular embodiments, the minimum length may be a fixed duration, such as about ⅓ sec (i.e., corresponding to an IHR of at most 180 BPM), or at least a target minimum percentage of a recent target interbeat interval, such as at least 65 percent of the smaller of either 1) the immediately preceding valid interbeat interval or 2) an interbeat interval corresponding to a recent baseline heart rate. If not, the candidate heart beat is declared invalid.

Candidate beats passing the "short duration" tests of the apparent noise unit 515 are forwarded to slope unit 520, which determines whether the absolute value of the slope of a plurality of interbeat intervals preceding the candidate heart beat interval is so large as to be outside the range of physiologically valid slopes and therefore invalid. In one embodiment, the slope unit determines the slope of the interbeat intervals for the candidate beat and the immediately preceding valid beat, and compares the slope to an upper slope threshold. In a particular embodiment, the slope unit determines if the absolute value of the slope is less than or equal to 0.3, although other thresholds, such as an adaptable threshold, may be used instead of a fixed threshold. If the slope exceeds the slope threshold, the candidate heart beat is discarded as invalid.

The candidate heart beats passing the one or more tests of heart beat validation unit 285 (e.g., physiologically plausible heart beat interval unit 505, apparent missed heart beat unit 510, apparent noise unit 515, and slope unit 520) are accepted as valid beats. Data for the valid beats (which may comprise time stamps of the valid beats and/or interbeat interval durations for each candidate beat and an immediately preceding beat, is forwarded to window analysis module 295.

In one embodiment, a finding of validity by any one or more of the units 505, 510, 515, and 520 can be used by a beat quality index module 286 to adjust the value of a beat quality index, as described above.

In one embodiment, as shown in FIG. 3C, if a candidate heart beat is found to be invalid by (i.e., failed a test associated with) one or more of the units 505, 510, 515, and 520, a constraint modification unit 287 determines if the candidate heart beat occurred at a time after the most recent prior valid heart beat that is greater than a constraint modification time threshold for the determination made by one or more of units 505, 510, 515, 520. For example, if the physiologically plausible heart beat interval unit 505 has a constraint modification time threshold of 5 sec, and at least 5 sec have elapsed since the last valid beat when a candidate heart beat is declared invalid, the constraint modification unit 287 would modify the constraint, such as by relaxing the constraint or tightening the constraint.

Turning now to FIG. 3D, a more detailed stylized depiction of the window analysis module 295 of FIG. 2, in accordance with one illustrative embodiment of the present invention, is depicted. The window analysis module 295 may receive various data from the heart beat validation module 285, such as time stamps of valid beats and/or interbeat interval durations. Based upon data from the heart beat validation module 285, the window analysis module 295 further tests the valid interbeat intervals to determine if they are suitable for use to detect seizure events. Valid beats suitable for use in detecting seizures (which, as noted earlier, may change from one window to another window) are provided to the foreground/background module 297.

In the depiction shown in FIG. 3D, data received from the heart beat validation module 285 is forwarded to first window unit 555 in window analysis module 295. First window unit 555 forms a first window for each valid beat, the window including the valid beat and one or more preceding beats. In some embodiments the first window is a time window, and in other embodiments the first window is a number-of-beats window. In a particular embodiment, first window unit 555 uses a 5 second, backward-looking time window bounded on the present end by a first valid beat being tested. First window unit 555 may also, in some embodiments, determine the number of beats in the window.

The first window from unit 555 is tested with one or more window tests in first window analysis unit 560. The window tests determine whether the first valid beat shows excessive dispersion in the context of previous heart beats. In one embodiment, the dispersion tests include at least one short-term HRV test of the first window. In one particular embodiment, the first window analysis unit 560 calculates a least-squares linear fit of the beats in the window, and also calculates the mean squared error of the least squares linear fit. The mean squared error (MSE) can be used as a short-term HRV measure and is compared to at least one HRV threshold. If the MSE exceeds the threshold, then the first valid beat is discarded as unsuitable for use in seizure detection because it produces unacceptably high dispersion when added to a stream of valid beats. In one embodiment, a fixed HRV threshold of 0.25 is used, and the first valid beat is discarded if the HRV exceeds 0.25. Other HRV thresholds, including adaptive thresholds that vary with time, patient status or environmental conditions, may also be used. In particular, nonlinear least squares fits of the data may be used instead of the linear least-squares fit, and other models of fitting data may also be used depending upon the computational constraints applicable to a particular medical device. Whatever the fit chosen, short-term HRV may be measured from the MSE, the rate of change in heart rate may be estimated from the slope of the fit, and the interbeat intervals in the window may be estimated from the fit. Any of these parameters can be measured as a simple measurement, with equal weighting to all time units or beat units in the window, or as an exponentially forgetting measurement.

First window analysis unit 560 may also perform additional window tests to assess the valid beats in the window. In one embodiment, the number of beats in the window is tested to determine whether the number of beats in the window exceeds a minimum number of beats threshold for the window. Since only valid beats passing the HRV test may be used to detect seizure events, there may be instances when declaring invalid of one or more beats compromises the accuracy of a seizure detection algorithm. Enforcing a minimum number of beats threshold may help to ensure that only periods with relatively good data are used for seizure detection. In addition to disqualified data, the number of beats threshold may also be used where noise or skipped beats occur but are not filtered with the testing performed in heart beat validation module 285. In one embodiment, the number of beats threshold may comprise a fixed integer number of beats, for example 2 or 3 beats. In another embodiment, a fractional threshold may be used corresponding to, for example, 50 BPM. In a still further embodiment, an adaptive threshold may be used that varies with time, patient status or condition, and environmental factors.

If the valid beat passes the one or more window tests of first window analysis unit 560, the beat is accepted as suitable for seizure detection and forwarded to foreground/background module 297. Otherwise, the valid beat is discarded and not used for seizure detection.

Turning now to FIG. 3E, a more detailed stylized depiction of the foreground/background module 297 of FIG. 2, in accordance with one illustrative embodiment of the present invention, is depicted. In one embodiment, the foreground/background module 297 may receive various data indicative of valid beats suitable for seizure detection from the window analysis module 295. This may include time stamp data for valid beats suitable for seizure detection, and/or fiducial time markers associated with such beats. Based upon data from the window analysis module 295, the foreground/background module 297 is capable of calculating a short-term indication of HR and a longer-term indication of HR for ultimate use in seizure identification module 299 to detect a seizure event.

Data from window analysis module 295 is received by foreground HR unit 565, which forms a second window for each of the valid beats suitable for seizure detection. The second window includes a first valid beat suitable for seizure detection and at least one prior valid beat suitable for seizure detection. The second window preferably includes a plurality of consecutive interbeat intervals. In one embodiment, the second window is a backward-looking time window bounded at one end by a first valid beat suitable for seizure detection and including at least one prior valid beat suitable for seizure detection. In one embodiment, the second window may be the same size is the first time window from module 555. In a particular embodiment, the window is a three second, backward-looking window, or an exponentially-forgetting window with comparable weighting. A relatively short foreground window advantageously tracks heart changes quickly, enabling faster detection of epileptic seizures. The window size may be optimized to balance the desire for fast seizure detection against potential false positive detection from relatively short-lived tachycardia phenomenon such as standing or sitting upright, climbing a flight of stairs, or sudden and transient exertion.

A foreground heart rate parameter for the second window is determined using a statistical measure of central tendency of heart rate (or interbeat intervals) for the beats (or intervals) in the second window. Commonly known measures of central tendency such as moving average, mean or median may be used in some embodiments. However, the present inventors have determined that an improved algorithm may be obtained by using as the measure of central tendency a target percentile value, for example a percentile in the range of the $20^{th}$ to the $80^{th}$ percentile, in a uniform distribution-based Percentile Tracking Filter applied to the valid beats in the second window. In a particular embodiment, the thirtieth ($30^{th}$) percentile of a uniform distribution Percentile Tracking Filter is used as the measure of central tendency for the sequence of successive valid interbeat intervals, updated each time the window validity test is satisfied for the moving window ending at the heart beat that was most recently determined valid. By using a percentile smaller than the $50^{th}$ percentile, the second window will more quickly track decreasing interbeat intervals, which corresponds to increases in heart rate (i.e. tachycardia) that are frequently associated with epileptic seizures. It should be noted that if the FHR parameter uses heart rate instead of interbeat intervals, the heart rate would track the $70^{th}$ percentile to track increases in heart rate faster than decreases because, as noted previously, heart rate and interbeat intervals are inversely related.

Parameters may also be used to describe the uniform distribution used in the Percentile Tracking Filter to improve performance of the algorithm. In particular, upper and lower bounds for the uniform distribution may be specified to improve the ability of the algorithm to more accurately track the target percentile used in the PTF. Additional parameters may also be used to provide a weighting factor to the PTF, including for example forgetting factors used to weight the HR to emphasize more recent heart beats more than prior beats. Such exponential forgetting may be used to adaptively track the recent minimum and maximum valid interbeat intervals and use these as adaptive parameters describing the uniform distribution used by the PTF. Persons of skill in the art, provided with the present disclosure and a knowledge of the prior art, will appreciate that other models may be used in the PTF for the time-varying distribution of interbeat intervals, as described in U.S. Pat. No. 6,768,968, U.S. Pat. No. 6,904,390, and U.S. Pat. No. 7,188,053, previously incorporated by reference.

Returning to FIG. 3E, data from window analysis module 295 is also used in background HR unit 567, which forms a third window for each of the valid beats suitable for seizure detection. The third window includes the first valid beat suitable for seizure detection from the second window and at least two prior valid beat suitable for seizure detection, and is used to provide a longer-term ("background") measure of HR than the second (foreground) window. In one embodiment, the third window is a backward-looking time window that is longer than the second window, bounded at the present end by the first valid beat from the second window.

In a particular embodiment, the third window is a 500 second window, or an exponentially forgetting window with time weighting on a timescale of 500 sec, bounded on the present side by the first valid beat from the second window. The third window size may be made larger or smaller to smooth our or reveal local perturbations of patient HR. In many embodiments, it may be desirable to smooth small-scale fluctuations in HR, such as those associated with transient tachycardia events previously discussed (e.g., standing, sitting upright, climbing stairs, sudden exertion).

A background HR parameter for the third window is obtained using a statistical measure of central tendency of heart rate for the beats in the third window. As noted regarding the foreground HR parameter, a number of measures of central tendency (e.g., mean, median) may be used. In one embodiment, a target percentile value (for example, a value in the range from the $30^{th}$ percentile to the $70^{th}$ percentile) in a uniform distribution Percentile Tracking Filter applied to the valid beats in the second window is used as the measure of central tendency. In a particular embodiment, the fiftieth ($50^{th}$) percentile of a uniform distribution Percentile Tracking Filter is used as the measure of central tendency. In one particular embodiment, the Percentile Tracking Filter is an exponentially forgetting Percentile Tracking Filter. Other types weighted and unweighted Percentile Tracking Filters or other measures of central tendency may be used.

Upper and lower limits or bounds for the uniform distribution used in the background Percentile Tracking Filter may be provided. In some embodiments these limits may be adaptively determined based upon the maximum and minimum value of the beat intervals in the second relatively short window such a moving average (mean) or median.

The foreground HR and background HR values determined in units 565 and 567 may in some embodiments be forwarded to seizure identification module 299 without further processing in foreground/background module 297. In other embodiments, foreground/background module 297 performs additional calculations. In particular, an instantaneous heart rate calculation unit 569 may determine an IHR for every valid beat suitable for seizure detection. Certain embodiments of the invention may also include a short-term HR threshold unit 571 which determines a time duration that the IHR determined by calculation unit 569 continuously exceeds a short-term HR threshold. If the IHR continuously exceeds the short-term HR threshold for a short-term duration threshold, a seizure event may be declared as occurring. Alternatively, the IHR continuously exceeds the short-term HR threshold for the short-term duration threshold may be required in addition to the RHR threshold determined in module 299.

In certain embodiments, the invention may also comprise a slope duration calculation unit 573. This unit determines the instantaneous slope of HR (ISHR) and compares the slope to a short-term HR slope threshold. If the ISHR exceeds the short-term HR slope threshold for a slope duration threshold, a seizure event may be declared on that basis alone, or may be required in addition to the RHR exceeding its threshold determined in module 299. The foreground/background module 297 need not perform all steps 565-573. Any steps the foreground/background module 297 performs may be in any order, not necessarily that shown.

Although the IHR calculation unit 569, the short-term heart rate threshold unit 571, and the slope duration calculation unit 573 are shown in FIG. 3E as components of foreground/background module 297, in various other embodiments, one or more of these units can be included in other modules, such as window analysis module 295.

Turning now to FIG. 3F, a more detailed stylized depiction of the seizure detection module 299 of FIG. 2, in accordance with one illustrative embodiment of the present invention, is depicted. The seizure detection module 299 may receive various data from the foreground/background module 297, including, for example, the foreground HR parameter and the background HR parameter. Based upon data from the foreground/background module 297, the seizure detection module 299 is capable of identifying a seizure event, such as described above.

In the exemplary depiction shown in FIG. 3F, data received from the foreground/background module 297 is forwarded to a relative heart rate (RHR) determination unit 587, which determines one or more relationships between two or more of the FHR, the BHR, the instantaneous heart rate (IHR), the short-term heart rate threshold, the short-term heart rate duration threshold, the ISHR, the short-term HR slope threshold, and the slope duration threshold. In a preferred embodiment, the RHR determination unit determines at least a RHR, although as discussed above any number of additional HR parameters and thresholds for such parameters may be determined and forwarded to seizure identification unit 589, which determines from one or more of the calculated values, the relationships, or both whether a seizure is identified.

In one embodiment, seizure identification unit 589 determines whether or not a seizure has based upon whether the RHR exceeds a seizure threshold value. The RHR is compared to the seizure threshold, and whether the RHR exceeds the RHR threshold is determined A signal indicative of the occurrence of a seizure event is provided based upon the comparison. In one embodiment, the threshold may be a fixed numerical threshold. The seizure threshold value is preferably one that reflects heart rate changes typically seen for the patient's seizure. In patients whose seizures are accompanied with tachycardia (accelerated heart rate), the seizure threshold is greater than one. Because the foreground heart rate is collected over a shorter time window than the background heart rate, a threshold greater than one reflects an increase in a short term heart rate over a baseline, long term heart rate. In one embodiment, the seizure threshold value is 1.3. For patients experiencing bradycardia in conjunction with seizures the threshold is less than one (or alternatively the BHR/FHR ratio is used instead of FHR/BHR). On the other hand, if the patient's seizures are accompanied with bradycardia (reduced heart rate), the threshold is generally less than one. The precise value of the threshold can be set by a physician in consultation with the patient, and may be periodically adjusted. It will be appreciated that for bradycardia-based detection, detections occur when the FHR/BHR ratio is below the threshold (or BHR/FHR is above the threshold) and the duration constraint is time spent at or below the threshold.

In one embodiment, an adaptive seizure threshold is used, and is determined based upon the actual ratio of the FHR and the BHR experienced by the patient during one or more seizure events. In another embodiment, the threshold may adaptively change based upon one or more variables such as the patient's level of exertion, the time of day, the number of false positive seizure detections (i.e., detection events that do not correspond to an actual seizure event), the number of false negative seizure detections (i.e., actual seizures for which no corresponding detection event occurred, changes in the patient's disease state, whether the patient is engaged in a high-risk activity such as swimming or driving, etc As noted above, generation of a seizure occurrence signal may depend upon more than the RHR alone exceeding a threshold. For example, the logic associated with generating the seizure occurrence signal may require that the RHR exceed the seizure threshold for a specified duration. In addition or alternatively, the seizure detection logic may require that a short-term HR parameter (such as IHR or the FHR) must exceed a short-term HR threshold (e.g., a fixed threshold of 110 BPM or an adaptive short-term threshold of an increase of 30 BPM from the BHR value at the time the RHR exceeded its seizure threshold) before the signal is generated. Additional thresholds for instantaneous slope and the duration of an instantaneous slope measurement exceeding a threshold may also be required.

If a seizure is identified by seizure identification module 299, in one embodiment, a response may be implemented. Based upon the identification, the medical device 200 may initiate one or more of several responsive actions, including generating an indication of at least one of a seizure or an impending seizure. This indication may be stored internally and/or externally, e.g., in the memory 217 (FIG. 2). This indication may also be transmitted to an entity separate from the medical device 200, e.g., to the monitoring unit 270 or monitoring and treatment unit 610 (FIG. 4), and stored, e.g., into the local database unit 255 and/or the database unit 250 (FIG. 2). The medical device 200 may initiate other responsive actions such as providing an audible, visible, or tactile alert to the patient or a caregiver; logging a timestamp of the seizure; initiation of a seizure severity determination routine based upon data from the heart beat/interval determination module 275, the foreground/background module 297, and/or the seizure detection module 299; communicating with one or more of database unit 250 or remote device 292, or notifying emergency services via email or autophone communications. It may be appreciated that, based upon the identification of a seizure by the seizure detection module 299, responsive action(s) may be performed by either the MD 200, monitoring unit 270, or other devices such as remote device 292.

In another embodiment, a preventive therapy or an interventive therapy may be performed as a responsive action. The therapy may comprise, for example, an electrical stimulation of the vagus nerve 127.

Figure 4:
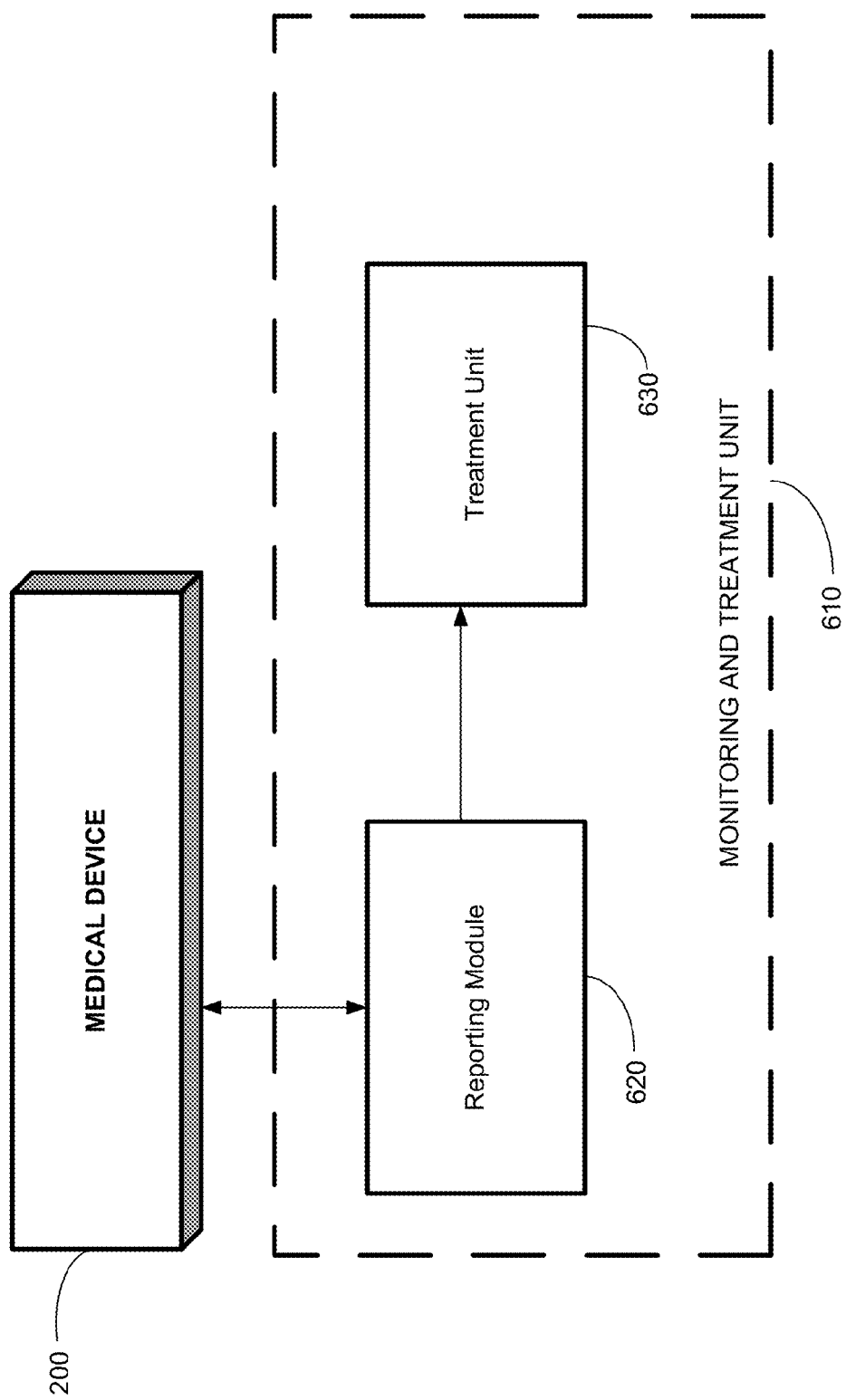
FIG. 4 is a block diagram of a monitoring and treatment unit, in accordance with one illustrative embodiment of the present invention.

Alternatively or in addition to detecting a seizure and providing a signal indicating its occurrence, according to one embodiment of the present invention as shown in FIG. 4, a monitoring and treatment unit 610, which may be a monitoring unit 270 or a unit other than medical device 200 implanted in or attached to an external portion of the patient's body, is provided. The monitoring and treatment unit 610 may comprise a reporting module 620 to receive an indication of an occurring or impending epileptic event from the medical device 200 and a treatment unit 630 that can provide a therapy, such as an electrical signal to a neural structure of a patient, a drug delivery device, or a device that can cool a neural structure of a patient. In one embodiment, the medical device 200 may be external to the patient's body and the monitoring and treatment unit 610 may comprise a wholly or partially implanted system. More specifically, treatment unit 630 may be an implanted unit with programmed electrical parameters (e.g., amplitude, pulse width, frequency, on-time, off-time, etc.) that defines a therapeutic stimulation signal provided by a stimulation unit 220 (FIG. 2B) to the electrodes 128 via the leads 201 (FIG. 2B). Reporting module 620 may be implanted or external to the patient's body.

Figure 5:
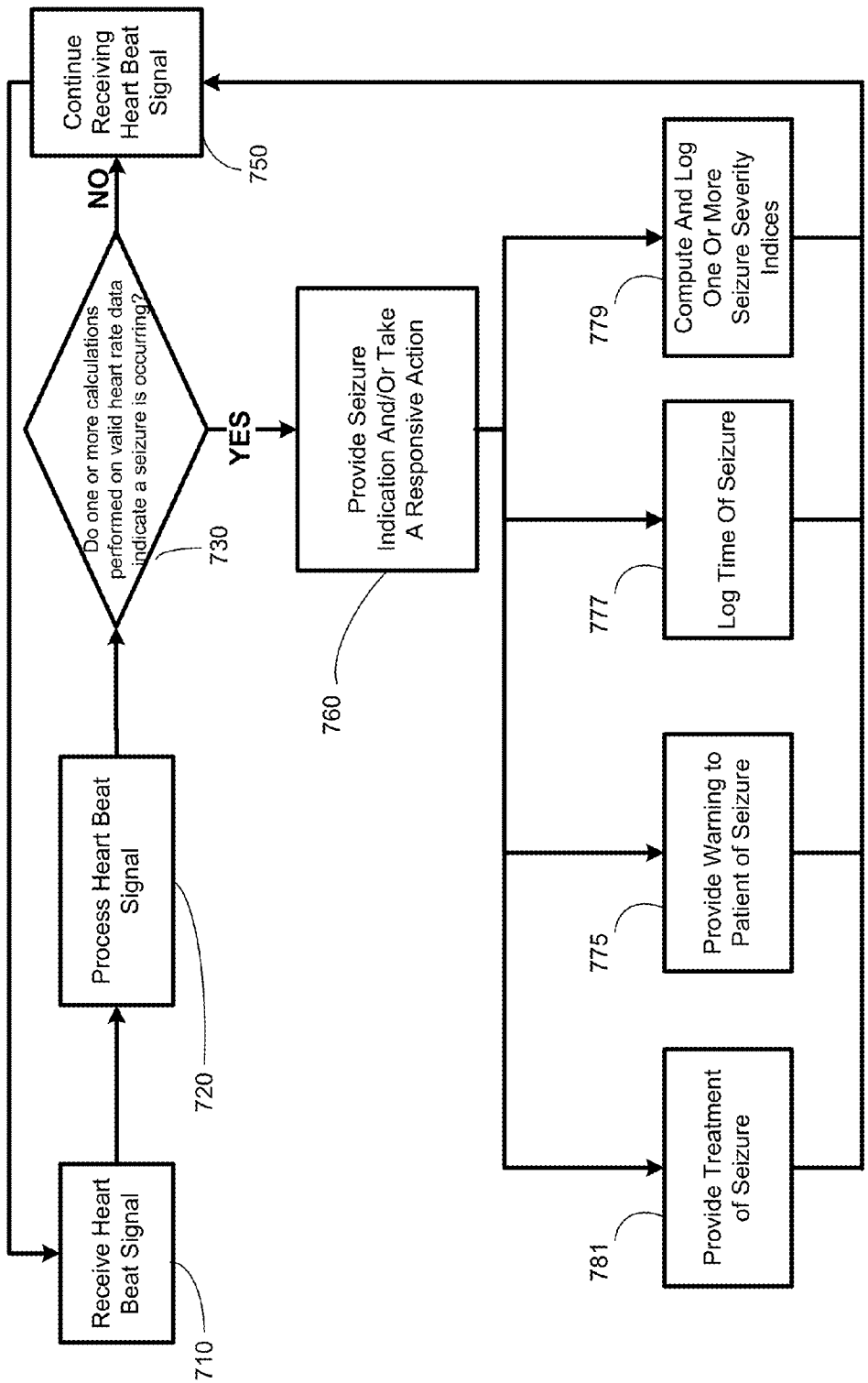
FIG. 5 illustrates a flowchart depiction of a method for detecting a seizure event and taking one or more responsive actions, in accordance with an illustrative embodiment of the present invention.

Turning now to FIG. 5, a stylized flowchart depiction of detecting a seizure event, in accordance with one illustrative embodiment of the present invention, is provided. The medical device 200 receives a heart beat signal (block 710). Typically, the cardiac data collection module 265 (FIGS. 2 and 3A) of the medical device 200 receives the heart beat signal. After performing buffering, amplification, filtering, and A/D conversion of the heart beat signal, the heart beat/interval determination module 275 and window analysis module 295 processes the heart beat signal to derive valid beat data (block 720). From the valid beat data, it is decided from one or more calculations if seizure is occurring (block 730). This decision may be performed by seizure identification module 299. A more detailed description of the step of deciding if the seizure is occurring is provided in FIG. 6 and the accompanying description below.

Based upon the decision (block 730), if no seizure is occurring, the medical device 200 continues to receive the heart beat signal (block 750, returning flow to block 710).

However, if the medical device 200 decides a seizure is occurring in block 730, the medical device 200 or an external unit 270 may provide an indication of the seizure occurrence and/or take a responsive action (block 760), such as providing a warning to the patient or his or her caregivers, physician, etc. (block 775); logging a time of seizure (block 777); computing and optionally logging one or more seizure severity indices (block 779); and/or providing treatment of the seizure (block 781).

The warning 775 may manifest as a warning tone or light implemented by a nearby object adapted to receive the indication of a seizure event from the medical device 200; an automated email, text message, telephone call, or video message sent from the medical device 200, either directly or via an monitoring unit 270, to the patient's cellular telephone, PDA, computer, television, etc. Such a warning may allow the patient or his or her caregivers to take measures protective of patient's well-being and those of others, e.g., pulling out of traffic and turning off a car, when the patient is driving; stopping the use of machinery, contacting another adult if the patient is providing childcare, removing the patient from a swimming pool or bathtub, lying down or sitting if the patient is standing, etc.

The time of the seizure event may be logged 777 by taking a time stamp of the decision 730 and storing it in a memory of the medical device 200 or the external unit 270.

One or more seizure severity indices may be computed and logged 779 from valid beat data, such as the duration of elevation of a shorter time window heart rate above a baseline heart rate, a slope of a short time window heart rate, heart rate variability or the slope of heart rate variability in one or more time or number-of-beat windows, and/or an area under the curve of a short time window heart rate relative to a baseline heart rate, among others. Though not to be bound by theory, it is reasonable to conclude that, for at least some types of seizures, an increase in heart rate, slope of heart rate, heart rate variability, slope of heart rate variability, area under the curve of heart rate relative to baseline, etc. and the absolute and/or relative durations of such changes provide a reasonable approximation of seizure severity as it would be measured electroencephalographically, without the difficulty in collecting, storing, and analyzing the volume of EEG data required to calculate seizure severity under traditional measures of seizure severity. The seizure severity index or indices may be logged 779 as well.

Figure 6:
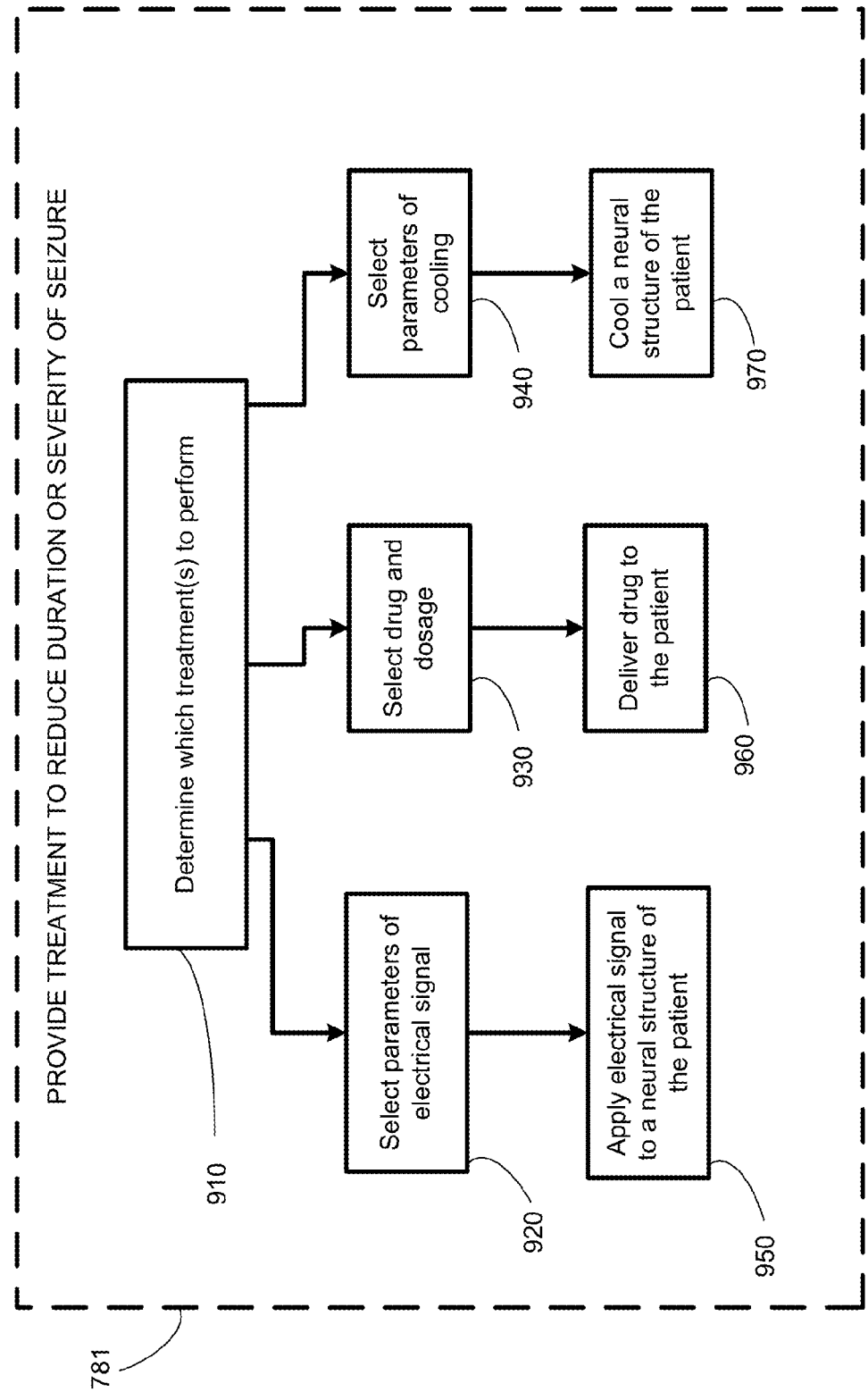
FIG. 6 illustrates a flowchart depiction of a treatment step of the method depicted in FIG. 5, in accordance with an illustrative embodiment of the present invention.

Turning now to FIG. 6 a stylized flowchart depiction of providing a treatment based upon identifying a seizure (blocks 760 and 781 of FIG. 5), according to one embodiment of the invention, is provided. In some embodiments, upon identifying a seizure, the medical device 200 determines which of a plurality of treatment(s) to perform (block 910). This determination is made based upon predetermined rules set up by a healthcare professional. The treatments may be one or more of electrical signal therapy, drug therapy, and/or neural cooling therapy.

With regard to an electrical stimulation treatment, the parameters of electrical signal therapy (including an "on time" of zero milliseconds, i.e., the application of no electrical signals) are selected (block 920). Similarly, the drug and dosage of drug therapy (including a dosage of zero milligrams, i.e., the application of no drugs) are selected (block 930) and the parameters of cooling a neural structure (including the maintenance of the ambient temperature of the neural structure, i.e., no cooling) are selected (block 940). Thereafter, the electrical signal, drug, or cooling are applied, delivered, or performed (blocks 950, 960, and 970). The combination of treatment, if any, may be determined based upon one or more values determined by the heart beat/interval determination module 275, heart beat validation module 285, the foreground/background module 297, or the seizure detection module 299.

Particular embodiments may combine or eliminate one or more of the treatment therapies available. Thus, a given device may comprise only electrical signal therapy, only drug delivery therapy, or combinations of any of the foregoing therapies.

Figure 7:
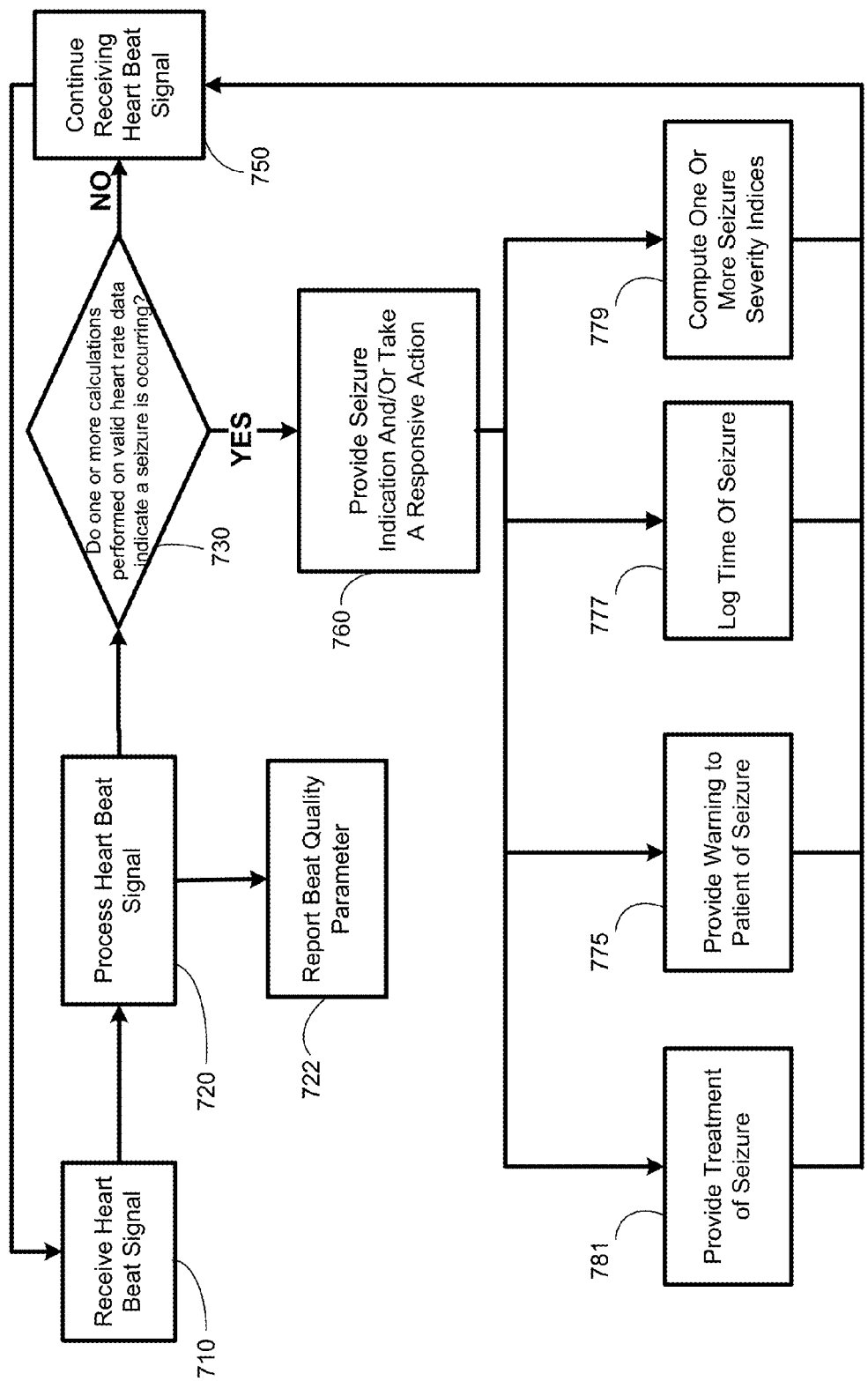
FIG. 7 illustrates a flowchart depiction of a method for detecting a seizure event and reporting a beat quality parameter, in accordance with an illustrative embodiment of the present invention.

Turning to FIG. 7, a stylized flowchart depiction of detecting a seizure event, in accordance with one illustrative embodiment of the present invention, is provided. Many elements of FIG. 7 are similar to like-numbered elements of FIG. 5, and the description of FIG. 5 is incorporated by reference in the context of FIG. 7. After performing buffering, amplification, filtering, and A/D conversion of the heart beat signal, the heart beat/interval determination module 275 and window analysis module 295 process the heart beat signal to derive valid beat data (block 720). From the valid beat data, the beat quality analysis module 276 calculates and reports a beat quality parameter (block 722).

The above methods may be performed by a computer readable program storage device encoded with instructions that, when executed by a computer, perform the method described herein.

All of the methods and apparatuses disclosed and claimed herein may be made and executed without undue experimentation in light of the present disclosure. While the methods and apparatus of this invention have been described in terms of particular embodiments, it will be apparent to those skilled in the art that variations may be applied to the methods and apparatus and in the steps, or in the sequence of steps, of the method described herein without departing from the concept, spirit, and scope of the invention, as defined by the appended claims. It should be especially apparent that the principles of the invention may be applied to selected cranial nerves other than, or in addition to, the vagus nerve to achieve particular results in treating patients having epilepsy, depression, or other medical conditions.

The particular embodiments disclosed above are illustrative only as the invention may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the invention. Accordingly, the protection sought herein is as set forth in the claims below.

What is claimed is:

1. A medical device system, comprising:
    a cardiac data collection module capable of collecting cardiac data comprising a fiducial time marker for each of a plurality of candidate heart beats in a first time series;
    a heart beat test module capable of performing a plurality of beat validity tests on each of said plurality of candidate heart beats in said first time series;
    a beat quality index module capable of determining a beat quality index value for each of said plurality of candidate heart beats, wherein the beat quality index value is based on the result of each beat validity test performed on the candidate heart beat;
    at least one responsive action module capable of performing at least one responsive action based upon an output of said beat quality index module, the at least one responsive action module selected from the group consisting of:
        a storage unit capable of storing a time series of beat quality index values;
        an event detection module capable of detecting at least one of an epileptic seizure event or an increased risk of an epileptic seizure event;
        a neurostimulation unit capable of applying a neurostimulation therapy to the patient; and
        a warning unit capable of providing a warning to at least one of a caregiver, the patient, or a physician based on an output of said beat quality index module.

2. The medical device system of claim 1, further comprising at least one sensor capable of receiving at least one signal related to a body parameter of a patient; and wherein said cardiac data collection module is capable of collecting cardiac data from said at least one signal.

3. The medical device system of claim 1, wherein said event detection module is capable of detecting an epileptic seizure event based on a first heart rate parameter determined from candidate heart beats in a first window, and a second heart rate parameter determined from candidate heart beats in a second window.

4. The medical device system of claim 1, wherein said neurostimulation unit is capable of:
    initiating a programmed neurostimulation therapy; and
    modifying a programmed neurostimulation therapy to obtain a second neurostimulation therapy and applying said second neurostimulation therapy to a target neural structure.

5. The medical device system of claim 1, wherein the at least one responsive action module is capable of modifying an earlier responsive action based upon an output of said beat quality index module.

6. The medical device system of claim 1, further comprising a library of beat validity tests, and wherein said heart beat test module is configured to implement at least one of said plurality of beat validity tests selected from said library of beat validity tests.

7. The medical device system of claim 1, wherein said storage unit is capable of storing beat quality index values for said plurality of candidate heart beats in said first time series as a second time series.

8. The medical device system of claim 1, wherein the beat quality index module is capable of:
setting the value of the beat quality index for a first candidate heart beat to a first integer value;
adjusting said value of the beat quality index for a first candidate heart beat to a second value, wherein adjusting comprises adding 1 to the first integer value, based on the heart beat test module performing at least one of:
a) determining that the interbeat interval falls within a range of physiologically plausible interbeat intervals;
b) determining that the interbeat interval is less than an upper interbeat interval threshold;
c) determining that the interbeat interval is greater than a lower interbeat interval threshold; or
d) determining that a slope of change between the interbeat interval and one or more preceding interbeat intervals falls within a range of physiologically plausible slopes of change.

9. The medical device system of claim 1, further comprising:
setting the value of the beat quality index for a first candidate heart beat to a first integer value;
adjusting said value of the beat quality index for said first candidate heart beat to a second value, wherein adjusting comprises adding 1 to the first integer value, based on the window analysis module performing at least one of:
a) determining that a dispersion of the candidate heart beats in said window is less than or equal to a predetermined dispersion threshold; or
b) testing whether said window contains a sufficient number of candidate heart beats determined to be within a range of physiologically plausible heart beats.

10. The medical device system of claim 1, wherein said neurostimulation unit is configured to apply vagus nerve stimulation therapy to said patient.

11. The medical device system of claim 1, wherein said heart beat test module comprises an interbeat interval module capable of determining an interbeat interval for a plurality of candidate heart beats in said first time series, based upon the fiducial time marker for the candidate heart beat and the fiducial time marker for a prior candidate heart beat.

12. The medical device system of claim 1, further comprising a heart beat validity module capable of determining whether a candidate heart beat is a valid heart beat based on the beat quality index value for the candidate heart beat.

13. The medical device system of claim 1, further comprising a window analysis module capable of performing a dispersion test on a plurality of heart beats in a window, wherein said window comprises one of a time window, a number of beats window, or an exponentially forgetting window having a first timescale.

14. The medical device system of claim 13, wherein said window is a backward-looking window comprising a plurality of candidate heart beats, wherein each candidate heart beat in the window has a beat quality index value exceeding a first threshold.

15. The medical device system of claim 13, wherein said event detection module is capable of determining the occurrence of an epileptic seizure event based upon a first heart rate parameter determined from candidate heart beats in a first window, and a second heart rate parameter determined from candidate heart beats in a second window.

16. The medical device system of claim 1, further comprising a window analysis module capable of determining a window beat quality index, said window beat quality index comprising a statistical measure of central tendency of individual beat quality indices for the candidate heart beats in said window.

17. A medical device system, comprising:
a cardiac data collection module capable of collecting cardiac data comprising a fiducial time marker for each of a plurality of candidate heart beats in a first time series;
a heart beat test module capable of performing a plurality of beat validity tests on each of said plurality of candidate heart beats in said first time series;
a beat quality index module capable of determining a beat quality index value for each of said plurality of candidate heart beats, wherein the beat quality index value is based on the result of each beat validity test performed on the candidate heart beat;
an event detection module capable of detecting an epileptic seizure event based on a first heart rate parameter determined from candidate heart beats in a first window, and a second heart rate parameter determined from candidate heart beats in a second window; and
at least one responsive action module capable of performing at least one responsive action based upon an output of said event detection module, the at least one responsive action module selected from the group consisting of:
a storage unit capable of storing a time series of beat quality index values;
a neurostimulation unit capable of applying a neurostimulation therapy to the patient; and
a warning unit capable of providing a warning to at least one of a caregiver, the patient, or a physician based on an output of said beat quality index module.

18. The medical device system of claim 17, wherein said neurostimulation unit is capable of:
initiating a programmed neurostimulation therapy; and
modifying a programmed neurostimulation therapy to obtain a second neurostimulation therapy and applying said second neurostimulation therapy to a target neural structure.

19. A medical device system, comprising:
a cardiac data collection module capable of collecting cardiac data comprising a fiducial time marker for each of a plurality of candidate heart beats in a first time series;
a heart beat test module capable of performing a plurality of beat validity tests on each of said plurality of candidate heart beats in said first time series;
a beat quality index module capable of determining a beat quality index value for each of said plurality of candidate heart beats, wherein the beat quality index value is based on the result of each beat validity test performed on the candidate heart beat;
an event detection module capable of detecting an epileptic seizure event based on a first heart rate parameter determined from candidate heart beats in a first window, and a second heart rate parameter determined from candidate heart beats in a second window; and a neurostimulation unit capable of applying a neurostimulation therapy to the patient, based upon an output of said event detection module.

20. The medical device system of claim 19, further comprising at least one responsive action module capable of performing at least one responsive action based upon an output of said event detection module, the at least one responsive action module selected from the group consisting of:

a storage unit capable of storing a time series of beat quality index values; and a warning unit capable of providing a warning to at least one of a caregiver, the patient, or a physician based on an output of said beat quality index module.

* * * * *